US008438663B2

(12) United States Patent
Wright

(10) Patent No.: US 8,438,663 B2
(45) Date of Patent: May 14, 2013

(54) FACE PROTECTOR LENS ASSEMBLY AND METHOD OF USE

(76) Inventor: Jerry Dean Wright, Pottsboro, TX (US)

( * ) Notice: Subject to any disclaimer, the term of this patent is extended or adjusted under 35 U.S.C. 154(b) by 176 days.

(21) Appl. No.: 13/081,699

(22) Filed: Apr. 7, 2011

(65) Prior Publication Data

US 2011/0179541 A1 Jul. 28, 2011

Related U.S. Application Data

(63) Continuation-in-part of application No. 12/950,846, filed on Nov. 19, 2010.

(60) Provisional application No. 61/263,765, filed on Nov. 23, 2009.

(51) Int. Cl.
*A61F 9/06* (2006.01)

(52) U.S. Cl.
USPC ..................................... 2/8.2; 2/8.8; 359/815

(58) Field of Classification Search ................ 2/8.1, 8.2, 2/8.3, 8.4, 8.5, 8.7, 8.8, 10, 424, 7, 6.3, 6.4, 2/6.5, 6.7, 15, 12, 427, 429, 434, 9, 430, 2/431, 13; 359/809, 805, 675, 815, 810, 359/361, 350, 355, 356, 357, 359
See application file for complete search history.

(56) References Cited

U.S. PATENT DOCUMENTS

| 2,180,216 A | * | 11/1939 | Snodgrass | 2/8.3 |
| 2,628,530 A | * | 2/1953 | Rabben | 351/44 |
| 2,799,862 A | * | 7/1957 | Rowe | 2/9 |
| 2,978,709 A | * | 4/1961 | Floyd | 2/9 |
| 3,112,490 A | * | 12/1963 | Malcom, Jr. | 2/8.7 |
| 3,415,595 A | * | 12/1968 | Nelson | 351/44 |
| 3,756,692 A | * | 9/1973 | Scott | 359/241 |
| 3,868,727 A | * | 3/1975 | Paschall | 2/8.5 |
| 4,047,249 A | * | 9/1977 | Booth | 2/10 |
| D264,891 S | | 6/1982 | Rosenius | |
| 4,707,860 A | * | 11/1987 | Holmstrom | 2/8.7 |
| 4,774,723 A | | 10/1988 | Ruck | |
| 5,191,468 A | * | 3/1993 | Mases | 359/361 |
| 5,673,431 A | * | 10/1997 | Batty | 2/9 |
| 6,006,366 A | * | 12/1999 | Vondrak | 2/424 |
| 6,151,711 A | | 11/2000 | Edwards | |
| D518,242 S | | 3/2006 | Wright et al. | |

(Continued)

OTHER PUBLICATIONS

Notification, International Search Report and Written Opinion dated Aug. 18, 2011 for PCT/US2010/057508.

*Primary Examiner* — Amy Vanatta
(74) *Attorney, Agent, or Firm* — Stephen C. Beuerle; Procopio, Cory, Hargreaves & Savitch LLP

(57) ABSTRACT

A lens assembly for securing in an opening in a face plate of a face protector has a first, retainer lens of shape and dimensions configured to be secured in the front opening of a face plate and having a curvature substantially matching the curvature of the face plate. A second lens of smaller dimensions is secured behind the first lens to provide a lens-in-a-lens configuration. The lens assembly may be releasably secured in the face plate opening and the second lens is interchangeable with sets of lenses having different properties such as lens shade. The retainer assembly has a back cover and a gasket or spacer between the back cover and second lens to allow second lenses of different depths to be secured in the assembly.

31 Claims, 22 Drawing Sheets

U.S. PATENT DOCUMENTS

| | | |
|---|---|---|
| D522,179 S | 5/2006 | Wright et al. |
| D526,094 S | 8/2006 | Chen |
| D526,097 S | 8/2006 | Lilenthal et al. |
| 7,168,095 B2 | 1/2007 | Wright |
| D539,988 S | 4/2007 | Crafoord et al. |
| D555,290 S | 11/2007 | Wright et al. |
| D557,460 S | 12/2007 | Jourde et al. |
| D558,403 S | 12/2007 | Lee et al. |
| D569,557 S | 5/2008 | Cho |
| D584,009 S | 12/2008 | Juhlin |
| D586,051 S | 2/2009 | Martin et al. |
| D624,705 S | 9/2010 | Wright |
| 2006/0010572 A1 | 1/2006 | Douglas |
| 2006/0272067 A1 | 12/2006 | Gagnon et al. |
| 2007/0192946 A1 | 8/2007 | Wright |
| 2007/0220649 A1 | 9/2007 | Huh |
| 2008/0060102 A1 | 3/2008 | Matthews et al. |

* cited by examiner

US 8,438,663 B2

FACE PROTECTOR LENS ASSEMBLY AND METHOD OF USE

CROSS-REFERENCE TO RELATED APPLICATIONS

The present application is a Continuation In Part of co-pending patent application Ser. No. 12/950,846 filed on Nov. 19, 2010, which claims the benefit of co-pending United States provisional pat. App. Ser. No. 61/263,765, filed Nov. 23, 2009, and the contents of each of the aforementioned applications are incorporated herein by reference in their entirety.

BACKGROUND

1. Field of the Invention

The present invention relates, in general, to lenses of face protectors, and, in particular, to lenses of welding masks or helmets.

2. Related Art

Welding helmets or masks are headgear used when performing certain types of welding to protect the eyes, face and neck from flash burn, ultraviolet light, sparks and heat. Welding helmets are necessary to prevent arc eye, a painful condition where the cornea is inflamed. Welding helmets can also prevent retina burns, which can lead to a loss of vision. Both conditions are caused by unprotected exposure to the highly-concentrated UV rays emitted by the welding arc (which can also damage uncovered skin, similar to a sunburn).

All welding helmets include a small window, called a lens, through which the welder looks at the weld. In older helmets, the window can be made of darkly tinted glass, or perhaps a pair of polarized lenses. In more modern helmet designs, transparent material that darkens automatically when exposed to the flare of a welding arc are more common. Either type, however, is susceptible to damages such as cracks that can compromise the protection from ultraviolet rays. In addition to the lens shade, the helmet has a shroud around the face to protect it from hot metal sparks generated by the arc.

The hot metal sparks generated by the arc can ignite flammable objects in the welding area. Because the welding helmets include a small window directly in front of the welder's eyes and have obstructed peripheral vision or even no peripheral vision, a welder may not recognize that the hot metal sparks generated in the area (e.g., to the sides) of the welder. The obstructed peripheral vision also prevents the welder from clearly seeing the future direction of their welding line, and they also may not see potential dangers such as people walking up to them from the side or objects moving or falling into their path.

SUMMARY OF THE INVENTION

To solve these problems and others, the present invention involves a lens-in-a-lens assembly that protects a users eyes (e.g., during welding), while also allowing peripheral vision.

In one embodiment, a lens assembly for a face plate of a face protector has a first, retainer lens of shape and dimensions configured to be secured in a front opening of the face plate and having a curvature substantially matching the curvature of the face plate, and a second lens of smaller dimensions secured behind the first lens to provide a lens-in-a-lens configuration, with the second lens configured to extend across the eyes of a wearer of the face protector and the first lens extending around the sides of the wearer's face to provide peripheral vision. The lenses may be of tinted glass or may be automatic darkening filter (ADF) lenses which darken automatically when exposed to increased light such as the flare of a welding arc, and one or both lenses may be selected from sets of interchangeable lenses having different shades.

In one embodiment, the second lens may be releasably secured behind the first lens by a retainer assembly having a rear retainer frame and a gasket between the retainer frame and second lens, and the rear retainer frame is secured to the first lens by one ore more releasable fasteners. This allows the second lens to be replaced by second lenses of different properties, while the flexible gasket allows second lenses of different depths to be secured in the assembly.

Other features and advantages of the present invention will become more readily apparent to those of ordinary skill in the art after reviewing the following detailed description and accompanying drawings.

BRIEF DESCRIPTION OF THE DRAWINGS

The details of the present invention, both as to its structure and operation, may be gleaned in part by study of the accompanying drawings, in which like reference numerals refer to like parts and in which.

DETAILED DESCRIPTION

Certain embodiments as disclosed herein provide for a face protector having a face plate with a front opening which extends across the eye region of a wearer and rearwardly around the sides of the face towards the ears, and a lens-in-a-lens assembly secured in the front opening.

After reading this description it will become apparent to one skilled in the art how to implement the invention in various alternative embodiments and alternative applications. However, although various embodiments of the present invention will be described herein, it is understood that these embodiments are presented by way of example only, and not limitation. As such, this detailed description of various alternative embodiments should not be construed to limit the scope or breadth of the present invention.

With reference to FIGS. 1-9, a first embodiment of a lens-in-a-lens assembly ("lens assembly") 100 of a face protector 105 will be described. In an exemplary embodiment, the face protector 105 is used in a welding application; however, in an alternative embodiments, the face protector 105 and/or face plate 110 is used in other applications such as, but not limited to, safety applications, commercial applications, do-it-yourself (DIY) applications, grinding, splash guard, sand blasting, food preparation, fork lift operations, tile cutting, wood cutting, wood chopping, face protection from flying particles, forced high pressure washing applications, during boat travel in sport leisure and commercial fishing, snowboarding, skiing, snowmobiling, hiking, hunting, paint ball, law enforcement, fire fighting, motorcycling, dune buggy or rails, ATV, air soft, spectator sports (e.g., NASCAR car racing, NFL/college football, NHL/college hockey), commercial activities such as airline industry, landscaping, and governmental activities such as military, lake patrols, etc.

Figure 3:
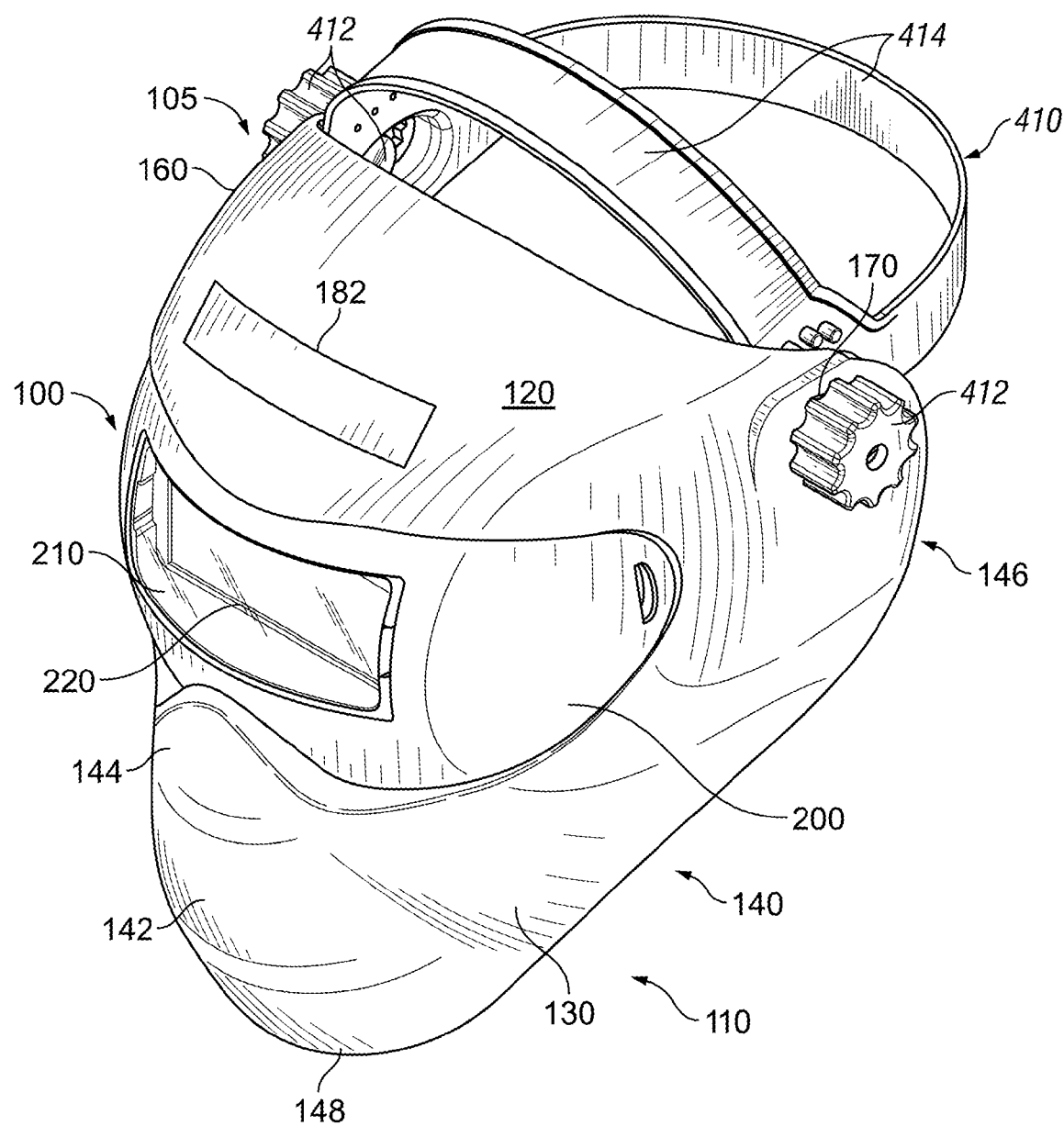
FIG. 3 is a front perspective view of the face protector and the lens assembly shown in FIGS. 1 and 2, with a strap assembly attached to hold the face protector in position on a user's head.
Figure 4:
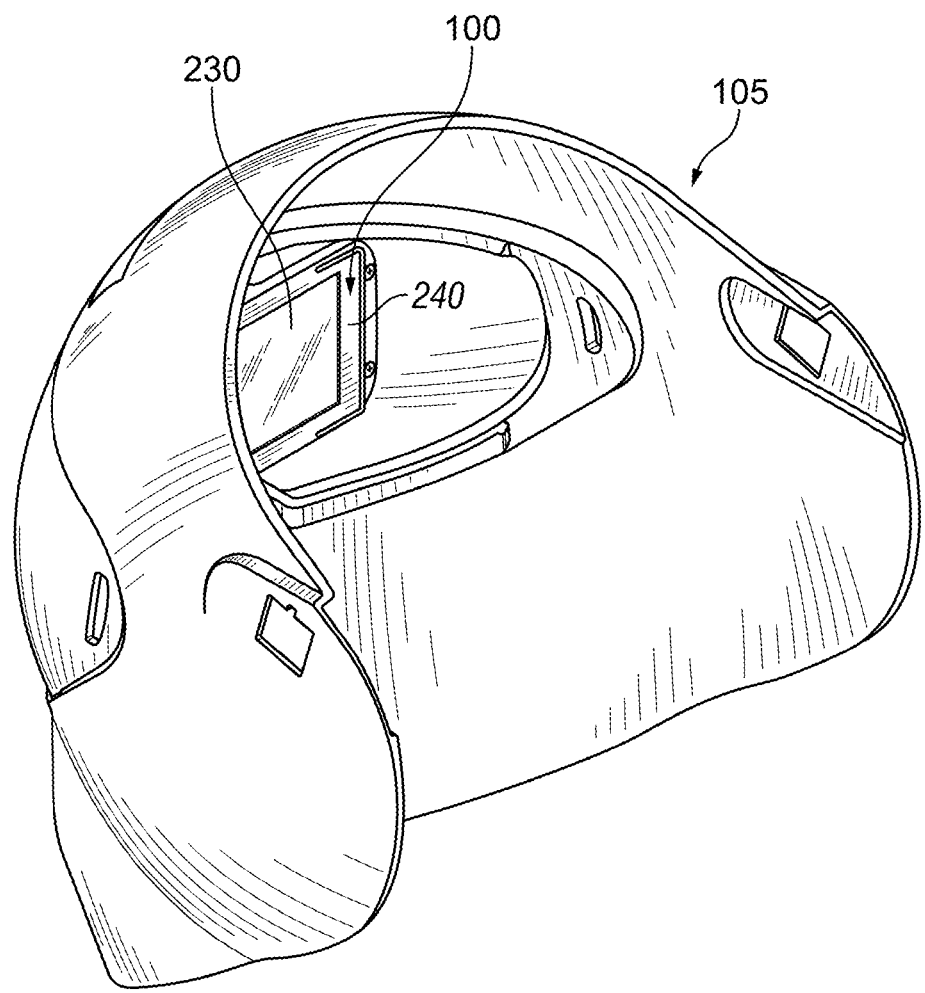
FIG. 4 is a rear perspective view of the face protector and the lens assembly shown in FIGS. 1 to 3.
Figure 5:
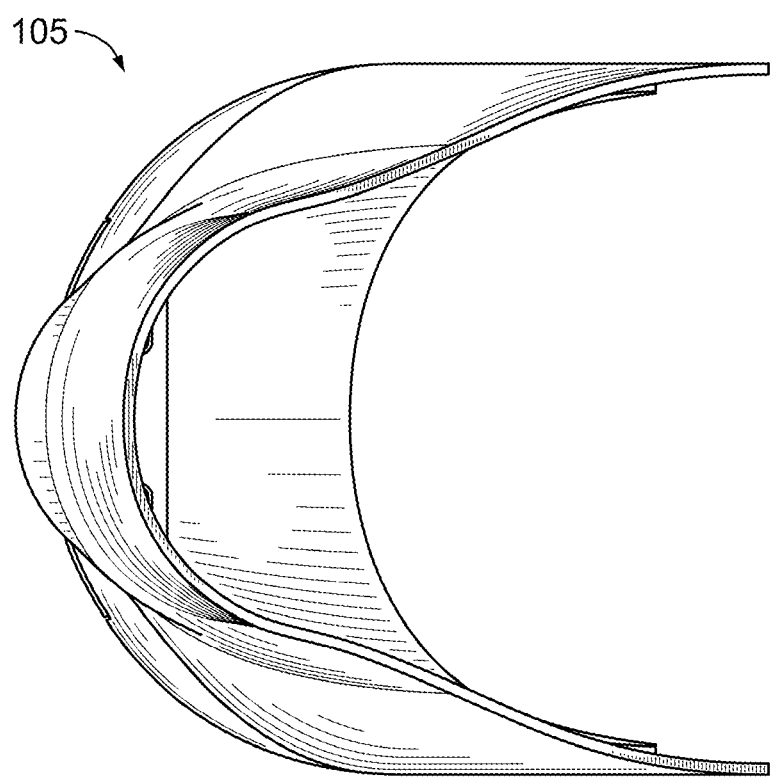
FIG. 5 is a bottom plan view of the face protector and the lens assembly shown in FIGS. 1 to 4.
Figure 6:
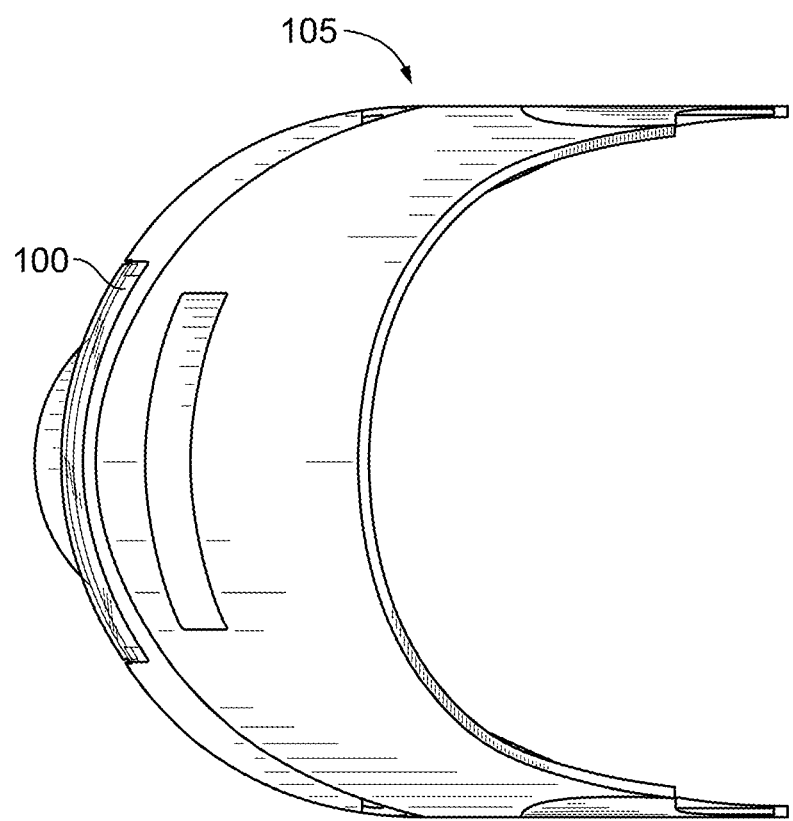
FIG. 6 is a top plan view of the face protector and the lens assembly shown in FIGS. 1 to 5.
Figure 7:
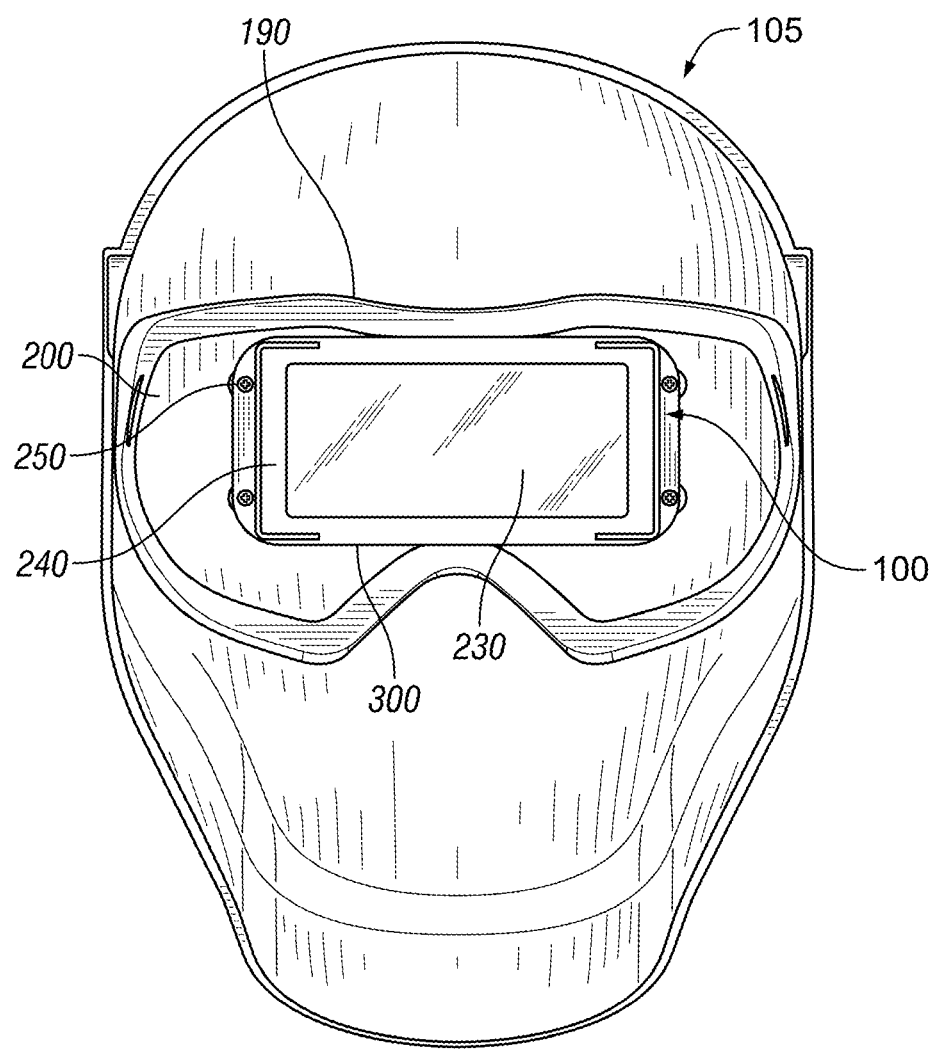
FIG. 7 is a rear elevational view of the face protector and the lens assembly shown in FIGS. 1 to 6.
Figure 8:
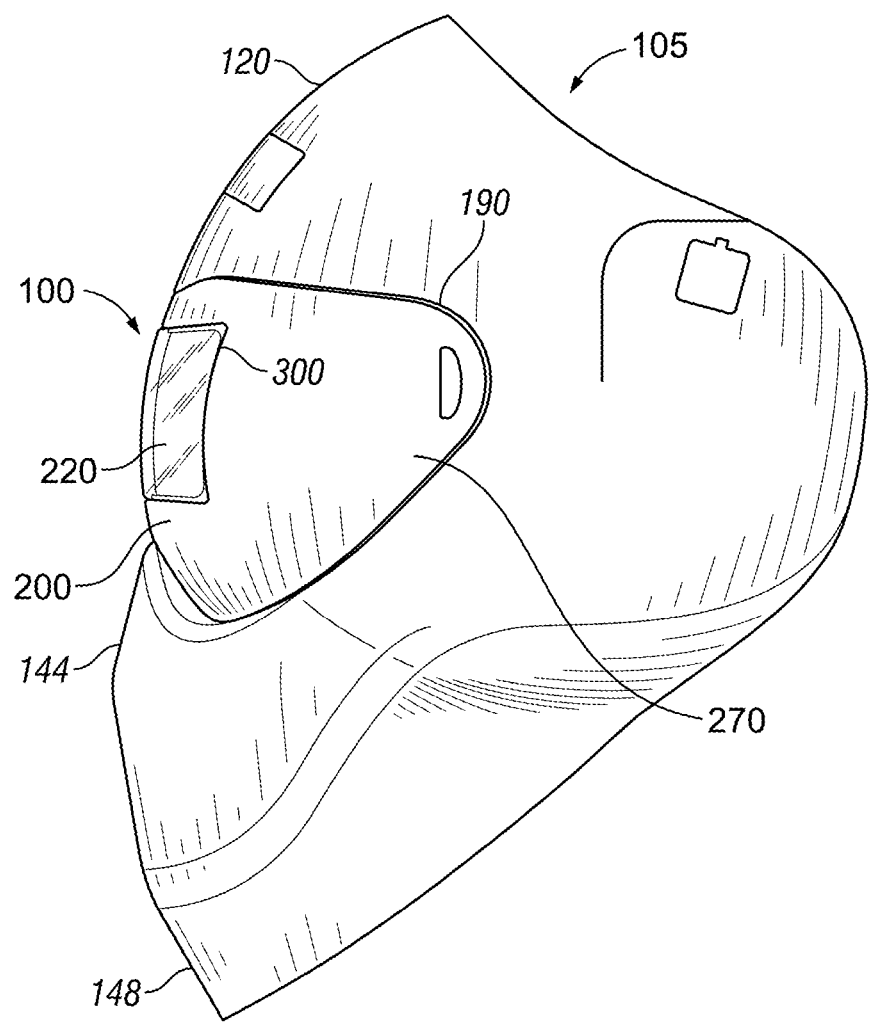
FIG. 8 is a right side elevational view of the face protector and the lens assembly shown in FIGS. 1 to 7, the left side elevational view being a mirror image thereof.

With reference to FIG. 3, before describing the lens assembly 100, the face protector 105 will be generally described. The face protector 105 protects the front of a user's head (i.e., forehead, face, eyes, cheeks, jaw, chin, mouth, nose, ears) from flash burn, ultraviolet light, sparks, heat, and/or other elements associated with the activity/application.

The face protector 105 includes a face plate 110 preferably made of an injection molded thin, plastic material. The face plate 110 has a configuration generally similar to the configuration of a human face and includes a forehead portion 120, a cheek portion 130, a jaw portion 140, a mouth portion 142, a nose portion 144, ear portions 146, a chin portion 148, and the replaceable/interchangeable lens assembly 100 that cover and protect the forehead, cheeks, jaw, mouth, nose, ears, chin, and eyes, respectively, of a user.

The forehead portion 120 is just wider than the width of the head of the user, is curved rearwardly, and extends from the brow area to just above the forehead area of the user. Substantially all of the skull is not covered by the forehead portion 120 or the rest of the face protector 110. Although not shown, in alternative embodiments, the forehead portion 120 may include one or more ventilation sections for ventilating the face protector 110. On a front side 160 of the forehead portion 120, the forehead portion 120 may include an insert and/or indicia 182 displaying a trademark, logo, or other insignia pertinent to the application of the face protector 110. The mold used to make the face protector 110 may include different mold inserts for the different indicia so that the same mold, but different mold inserts, may be used to manufacture the face protectors 110 for different applications.

The cheek portion 130 is curved rearwardly from the nose portion 144 and the mouth portion 142 of the face plate 110, and protects the cheeks of a user.

The jaw portion 140 is curved rearwardly from the mouth portion 142 and the cheek portion 130 of the face plate 110, and protects the jaw area of a user. The jaw portion 140 includes the chin portion 148, which has a cupped configuration for receiving the chin of a user. The jaw portion 140 decreasingly tapers in width from the top of the jaw portion 140, just below the lens assembly 100, to the bottom of the chin portion 148.

The mouth portion 142 is disposed between the nose portion 144 and the jaw portion 140, and protects the mouth of a user. Although not shown, in an alternative embodiment, the mouth portion 142 may include ventilation holes in the grooves shown or in other areas of the mouth portion 142 and/or nose portion 144. The mold used to make the face protector 110 may include different inserts for the different mouth and/or nose designs so that the same mold, but different inserts, may be used to manufacture the face protectors for different applications (e.g. face protectors with and without mouth/nose ventilation holes).

The front side of the nose portion 144 may bow outward and the rear side 162 of the nose portion 144 may be concave to accommodate the nose of the user. Although not shown, as discussed above, the nose portion 144 may include one or more ventilation holes in alternative embodiments.

Figure 1:
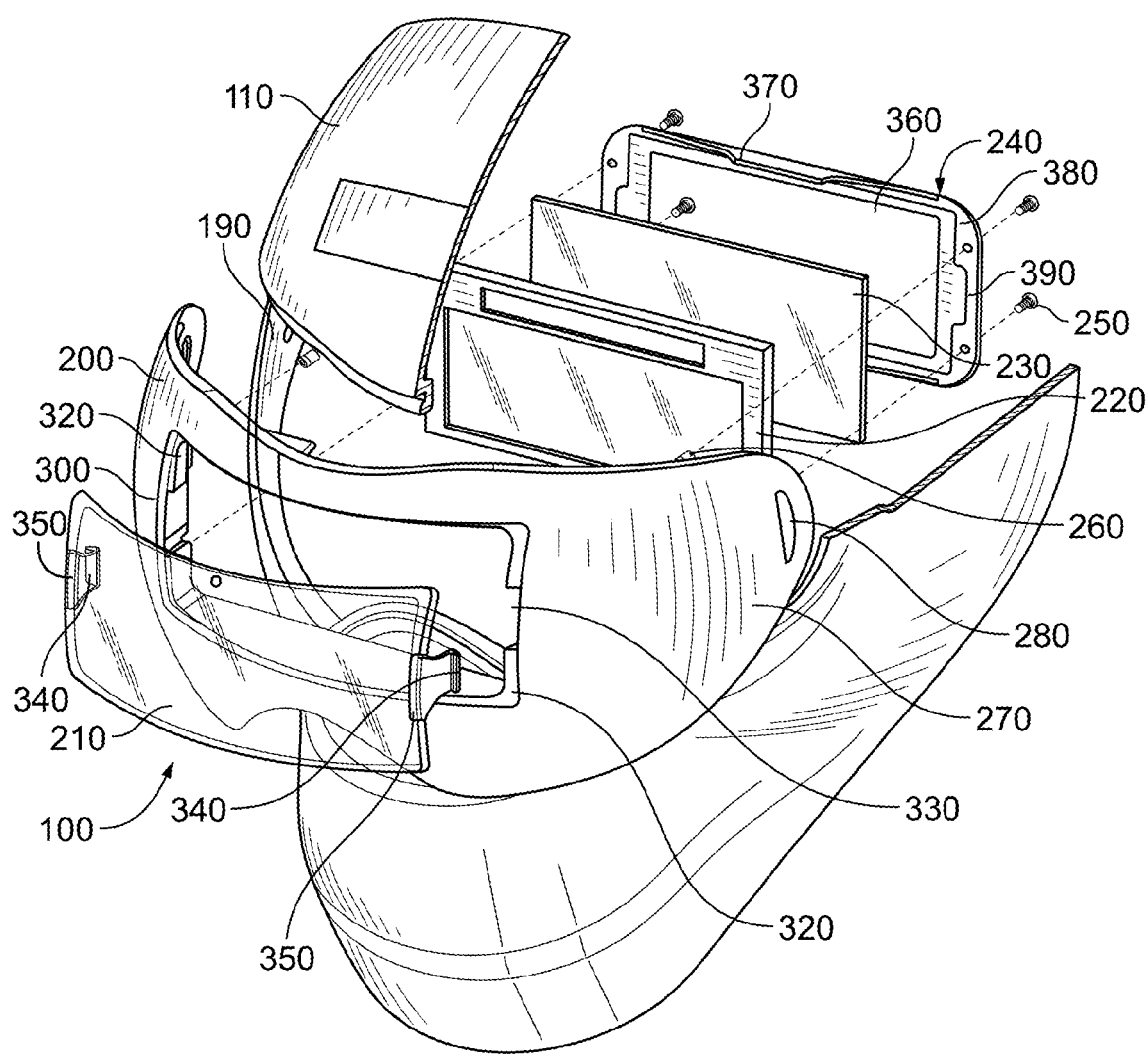
FIG. 1 is a front exploded and partially cut-away perspective view of an embodiment of a face protector with an embodiment of a lens assembly shown therein.
Figure 2:
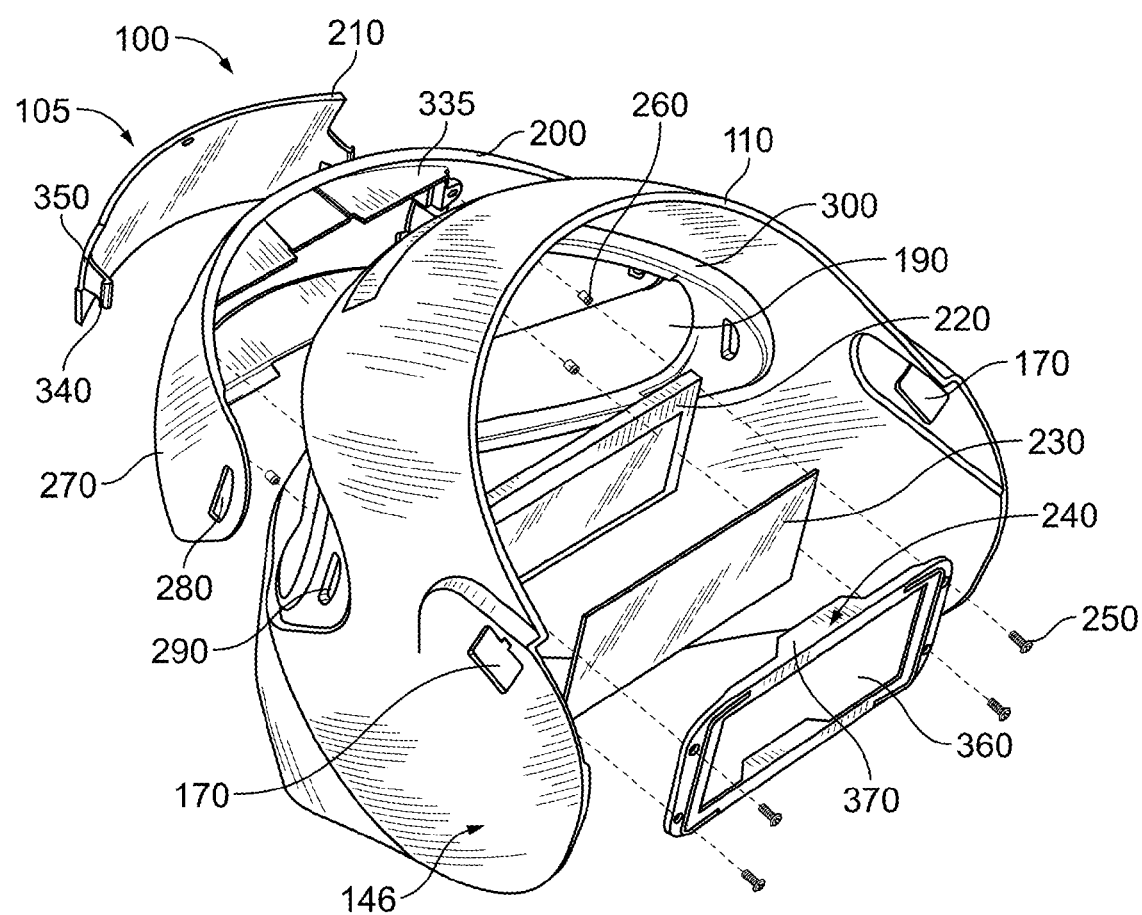
FIG. 2 is a rear exploded perspective view of the face protector and the lens assembly shown in FIG. 1.

The ear portions 146 extend rearwardly from the opposite ends of the lens assembly 100, and decreasingly taper in dimension progressing rearwardly, and protect the entire ears of the user. As illustrated in FIG. 2, substantially rectangular-shaped holes 170 are disposed in upper portions of the ear portions 146 for attaching a suitable strap assembly. FIG. 3 illustrates a strap assembly 410 with connectors 412 connected through the holes 170 in the back side of ear portions 146 of the face plate. Strap assembly 410 is used to retain face protector 100 in position on the user's head. The straps 414 of assembly 410 may be elastic or adjustable to accommodate a range of different size heads.

The face protector 110 may come in a one-size-fits-all configuration or may come in different sizes for different-sized heads (e.g., XL, L, M, S, child size).

An inner/back side of the face plate 110 may include cushion member(s) to provide added comfort to the user when wearing the face protector 105. The cushion member(s) may be affixed/connected to an inner/back side of the face plate 110 using an adhesive and/or fasteners. The cushion member(s) may be made of a waterproof, breathable material. The cushion member(s) may include holes therein to increase the breathability and comfort of the cushion member(s) when against the skin of the user. The cushion member(s), like the face plate 110, may come in different sizes to allow the user to custom fit the face protector 105 for the user's specific facial dimensions.

Because of the face-forming, low profile of the face plate 110, especially in the jaw portion 140, the face plate 110 allows the user to move one's head from side to side more easily because the lower jaw area of a normal welding helmet or mask hits the users shoulders and causes the helmet/mask to push up and/or off the user's face/head. Also, because of the rounded profile of the face plate 110, air flows better than other welding helmets because there is no 90-degree angle that the air has to move past. For example, the forehead portion 120 of the face plate 110 has a rounded profile compared to the 90-degree angles of other welding helmets. Also, because of the rounded spherical lens assembly 100, which will be described in more detail below, splatter, flying objects, and the like ricochet off the lens assembly 100 and face plate 110 with less impact and stress on the face plate 110, and the lens assembly 100 does not scratch so easily.

With reference generally to FIGS. 1-9, the lens assembly 100 will now be described in more detail. The lens assembly 100 protects the user's eyes from flash burn (e.g., causing arc eyes, retina burns), ultraviolet light, sparks, heat, and/or other elements associated with the activity/application. The lens assembly 100 also maximizes the user's general vision and peripheral vision, which helps the user to spot fires in the welding area (e.g., to the sides of the user) caused by hot metal sparks generated by the arc that ignite flammable objects.

The lens assembly 100 is replaceable/interchangeable with other lenses (e.g., for different welding applications, for different applications) and fits within an eye opening 190 (FIG. 1) of the face plate 110. The lens assembly 100 includes an Automatic Darkening Filter ("ADF") retainer lens 200, a front cover 210, an ADF lens 220, a polycarbonate lens protector 230, a back cover or rear retainer frame 240, flat head screws 250, and threaded inserts 260.

The ADF retainer lens 200 is partially spherical, toroidal, and/or cylindrical, providing the user with 180 degree viewing and unobstructed peripheral vision. Opposite peripheral/temple portions 270 of the ADF retainer lens 200 include crescent-shaped holes 280 that overlap crescent-shaped holes 290 in recessed eye opening section 300. Fasteners may extend through the holes 280, 290 for connecting the ADF retainer lens 200 to the recessed eye opening section 300 of the face plate 110. The ADF retainer lens 200 includes a central section with a rectangular opening 310 having front upper and lower recessed sections 320, side cut-outs 330, and rearwardly extending receiving section 335. The rearwardly extending receiving section 335 includes rearwardly extending upper horizontal member, lower horizontal member, and side vertical members that together form an air/space pocket between the ADF lens 220 and the front cover 210 when the lens assembly 100 is assembled. In one embodiment, the ADF retainer lens 200 is a #10 shaded lens and is made of polycarbonate. In alternative embodiments, the ADF retainer lens 200 is a shaded lens in the range of #2-#12 shaded lens.

The front cover 210 protects the ADF lens 220 from impact. The front cover 210 is transparent, un-shaded, rectangular/spherical/torical/cylindrical, made of polycarbonate and has a slight curved configuration/shape. Although front cover 210 is a separate component secured in an opening in the retainer lens in the illustrated embodiment, it may alternatively comprise a transparent or substantially transparent cover portion formed integrally with the retainer lens. The front cover 210, when disposed in the ADF retainer lens 200, is flush with the outer surface of lens 200. Rearward extending latch projections 340 extend from opposite sides 350 of the front cover 210 and extend through the side cut-outs 330 of the ADF retainer lens 200 (see FIGS. 1 and 2).

As indicated above, the lens assembly 100 has a lens-in-a-lens design with the ADF retainer lens 200 forming an outer holder lens and the ADF lens 220 forming an inner lens carried within/by the ADF retainer lens 200. Threaded inserts 260 are injected/added into a rear/back side of the ADF retainer lens 200.

The ADF lens 220 is substantially rectangular and has a rectangular frame portion and a rectangular lens portion held in the rectangular frame portion. In the embodiment shown, the ADF lens 220 is a 2 in.×4.25 in. ADF lens and is a shade #3 normally and darkens to shade #10 automatically when exposed to the flare of a welding arc. The ADF lens 220 is interchangeable with other 108 mm×50.8 mm×5 mm ADF filters and shades. In further embodiments, the outer ADF retainer lens 200 is a shade which matches the shade of the ADF lens 220, but these lenses may be of different shades in other embodiments. In an alternative embodiment, the ADF lens 220 is a 4 in.×4 in. or 4 in.×5 in. ADF lens, as described below in connection with the embodiment of FIGS. 10 to 15. In further embodiments, the ADF lens 220 and/or the outer ADF retainer lens 200 may be made of different shades and/or different types of ADF lenses.

A rectangular polycarbonate lens protector 230 is disposed behind the ADF lens 220.

The rectangular back cover 240 includes a central rectangular opening 360 and forwardly extending upper/lower flange members 370. A front of the back cover 240 includes a rectangular recessed section 380 with side cut-outs 390. The recessed section 380 in the front of the back cover 240 receives/retains the polycarbonate lens protector 230 and the ADF lens 220. The rearwardly extending latch projections 340 of the front cover 210 latch into the side cut-outs 390 of the back cover 240. The flat head screws 250 are inserted through holes in the corners of the back cover 240 and threadably engage the threaded inserts 260 in the rear side of the ADF retainer lens 200 to connect/assemble the rectangular back cover 240, the polycarbonate lens protector 230, and the ADF lens 220, the ADF retainer lens 200, and the front cover 210 of the lens assembly 100 together.

Thus, the lens assembly 100 protects the user's eyes from flash burn, ultraviolet light, sparks, heat, and/or other elements associated with the activity/application, and maximizes the user's peripheral/overall vision. Increased peripheral vision helps the user to spot fires or other objects in the welding area (e.g., to the sides of the user) caused by hot metal sparks generated by the arc that ignite flammable objects.

Figure 9:
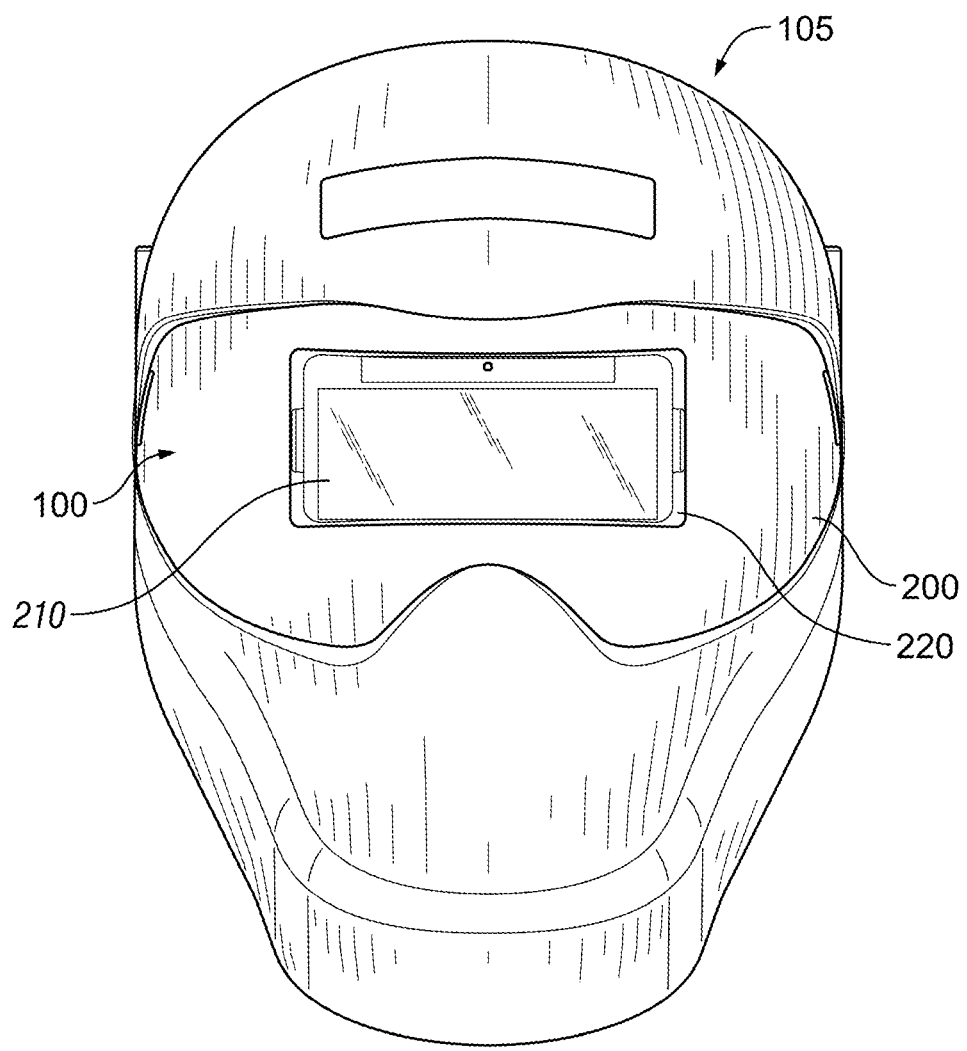
FIG. 9 is a front elevational view of the face protector and the lens assembly shown in FIGS. 1 to 8, the left side elevational view being a mirror image thereof.
Figure 10:
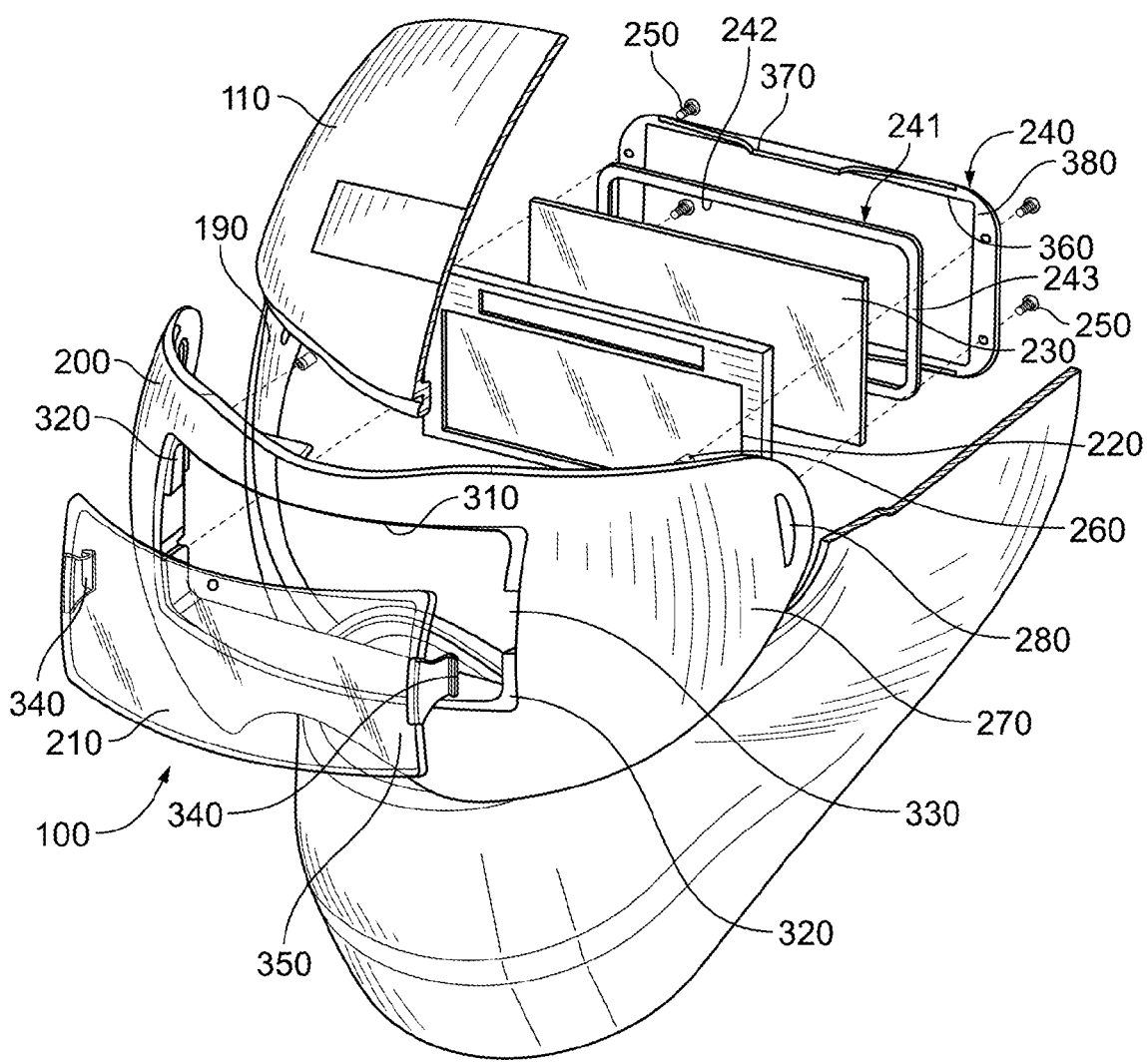
FIG. 10 is a front exploded and partially cut-away perspective view of the face protector of FIGS. 1 to 9 but with a modified lens assembly including a spacer gasket.
Figure 11:
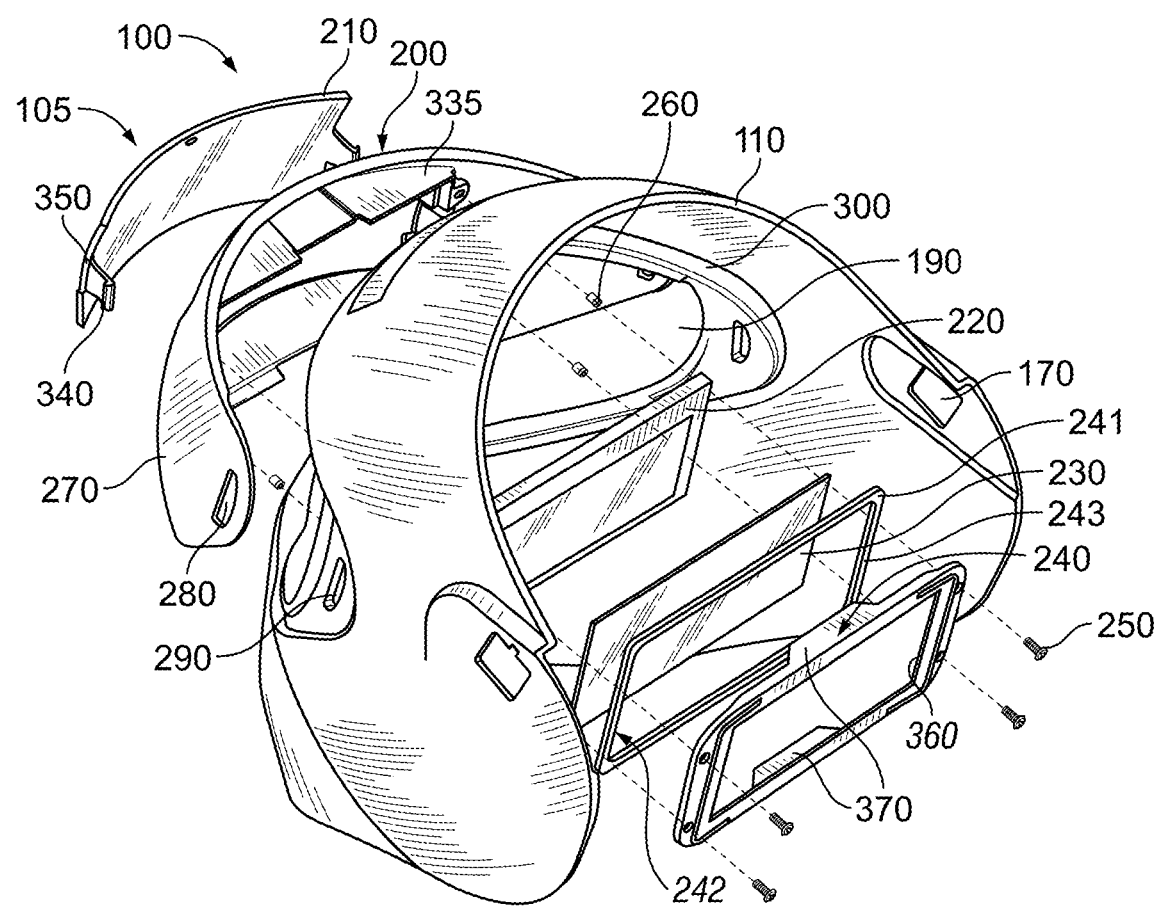
FIG. 11 is a rear exploded perspective view of the face protector and lens assembly of FIG. 10.
Figure 12:
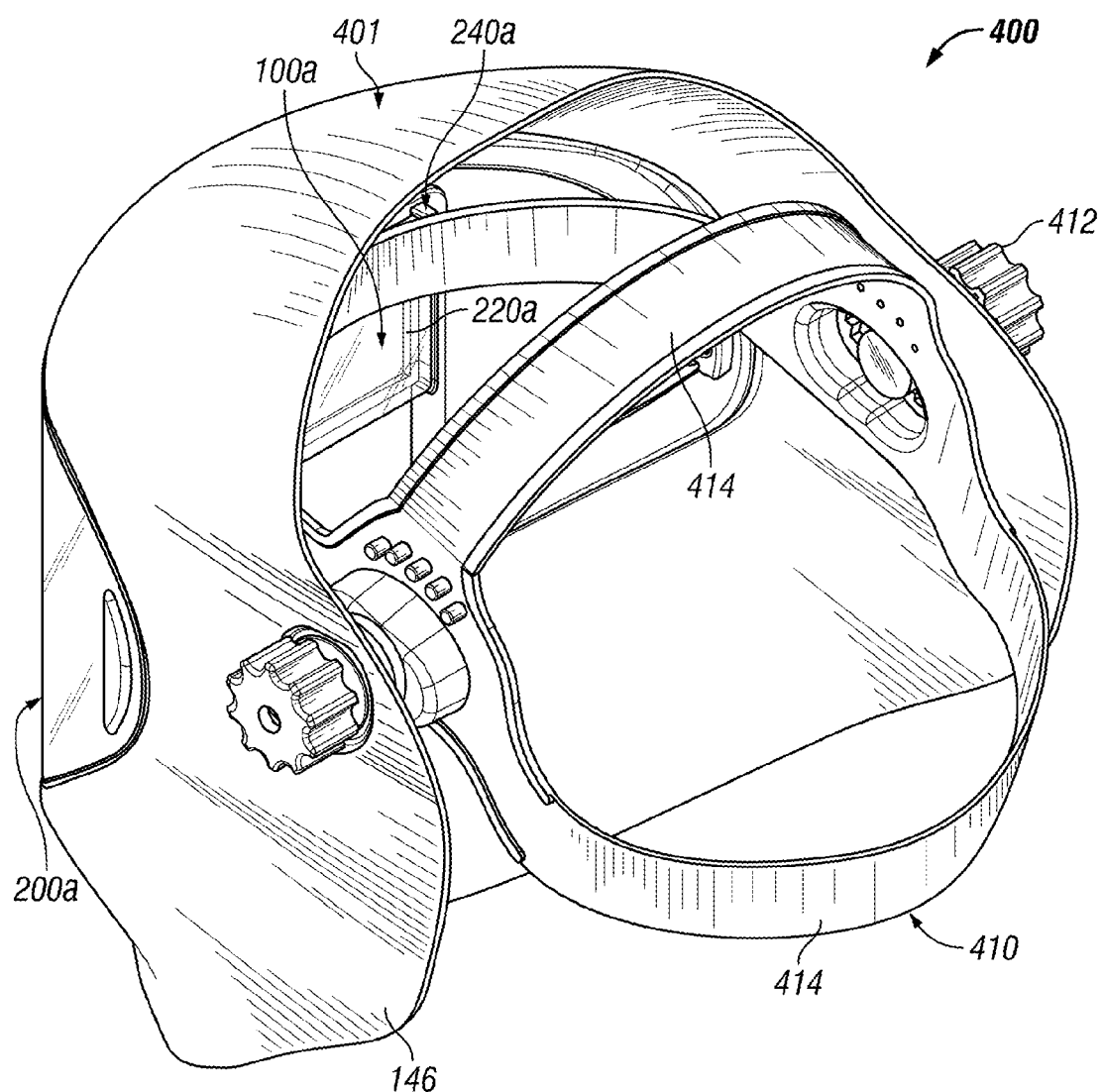
FIG. 12 is a rear perspective view of another embodiment of a face protector incorporating another embodiment of a lens assembly.
Figure 13:
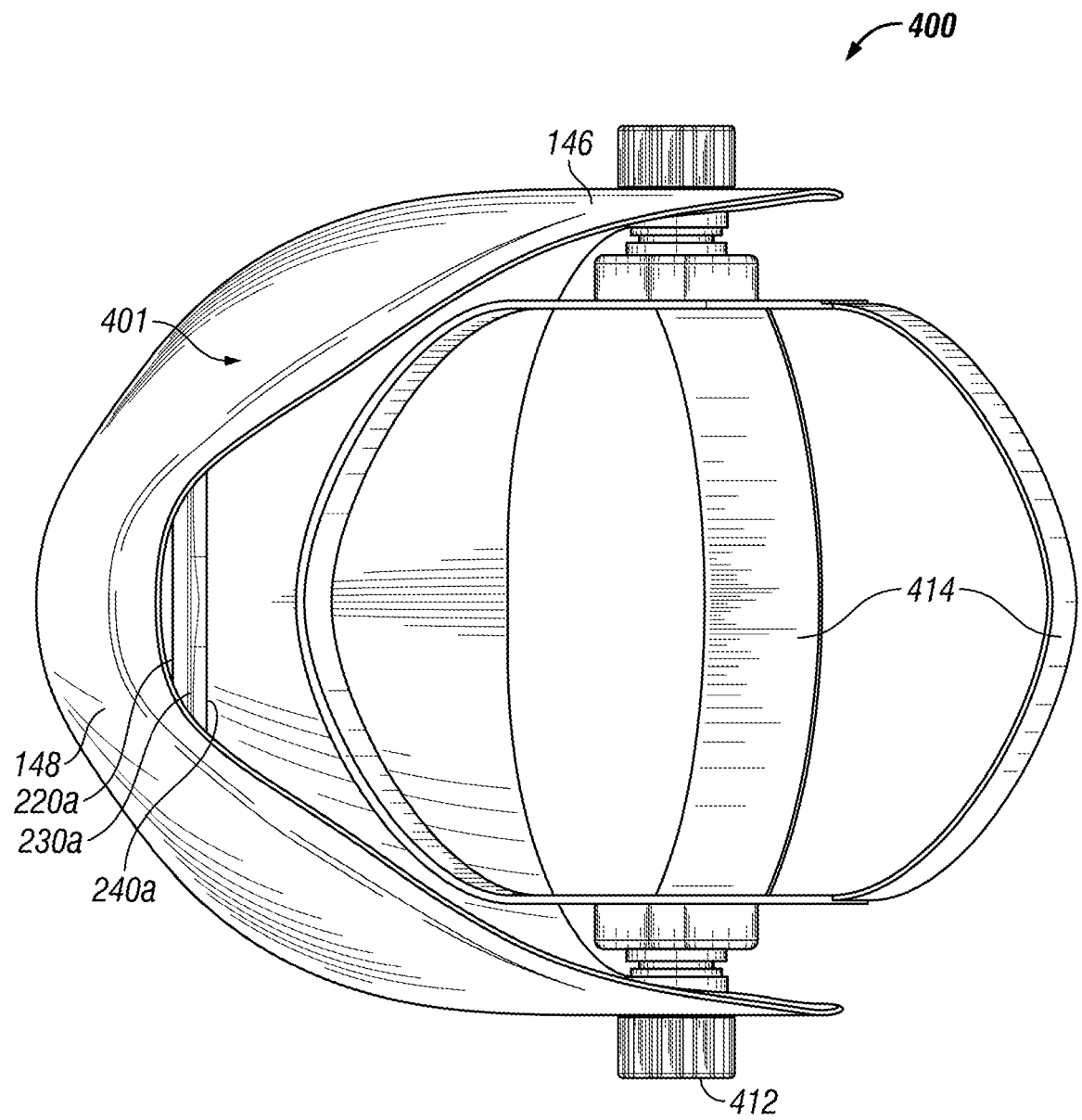
FIG. 13 is a bottom plan view of the face protector of FIG. 12.

FIGS. 10 and 11 illustrate a modification of the lens assembly 100 of FIGS. 1 to 9 in which a rear rectangular gasket or gasket plate 241 is added between the back cover or retainer 240 and the lens protector 230. Gasket 241 is of approximately the same dimensions as rear retainer or cover 240, and has a rectangular opening 242 of similar size aligned with opening 360. As illustrated in FIGS. 10 and 11, the opposite sides 243 of gasket 241 are inset relative to the sides 380 of rear cover 240 to allow clearance for fastener screws 250 when the components of the lens assembly are fastened together. The rear gasket 241 allows different ADF lenses 220 with different depths to be used in the lens assembly, for example generic ADF lenses. The rear gasket 241, back cover 230, and ADF lens 220 are held between back cover 240 and lens protector 230 by the screws 250 which secure back cover 240 to the threaded inserts in ADF retainer lens 200. The rear gasket 241 allows lens 220 to be exchanged for other ADF lenses 220 having different lens properties and/or different depths, as noted above. All other parts of the lens assembly are identical to the lens assembly 100 of FIGS. 1 to 9, and like reference numbers are used for like parts as appropriate.

FIGS. 12 to 17 illustrate a second embodiment of a face protector 400 comprising a face plate 401 having a front opening 402. A lens-in-a-lens assembly 100A which is similar to that of the previous embodiment but of different dimensions is mounted in front opening 402 in the same manner as described in the previous embodiment for lens assembly 100. Parts of assembly 100a which are equivalent to corresponding parts in the previous embodiment but of different dimensions or shape are provided with the same reference numbers as in the previous embodiment, followed by the letter A, and reference is made to the above description of these parts in the first embodiment for details of their materials and functions. The lens-in-a-lens assembly 100a and the front opening 402 for receiving the assembly are both larger in this embodiment than the previous embodiment, offering an increased viewing area to the wearer.

The face plate 401 is similar in shape and made of the same material as face plate 110 of the previous embodiment, and like reference numbers are used for like parts as appropriate. Reference is made to the description of these parts in connection with the previous embodiment, and the parts are not described in detail in connection with this embodiment, apart from any variations from the previous embodiment. A strap assembly 410 with connectors 412 which connect to the holes 170 in the back side of ear portions 146 of the face plate is illustrated in FIGS. 12 to 17, similar or identical to the strap assembly 410 secured to face protector 100 of the first embodiment, as illustrated in FIG. 3 above, and like reference numbers are used for like parts as appropriate.

Figure 14:
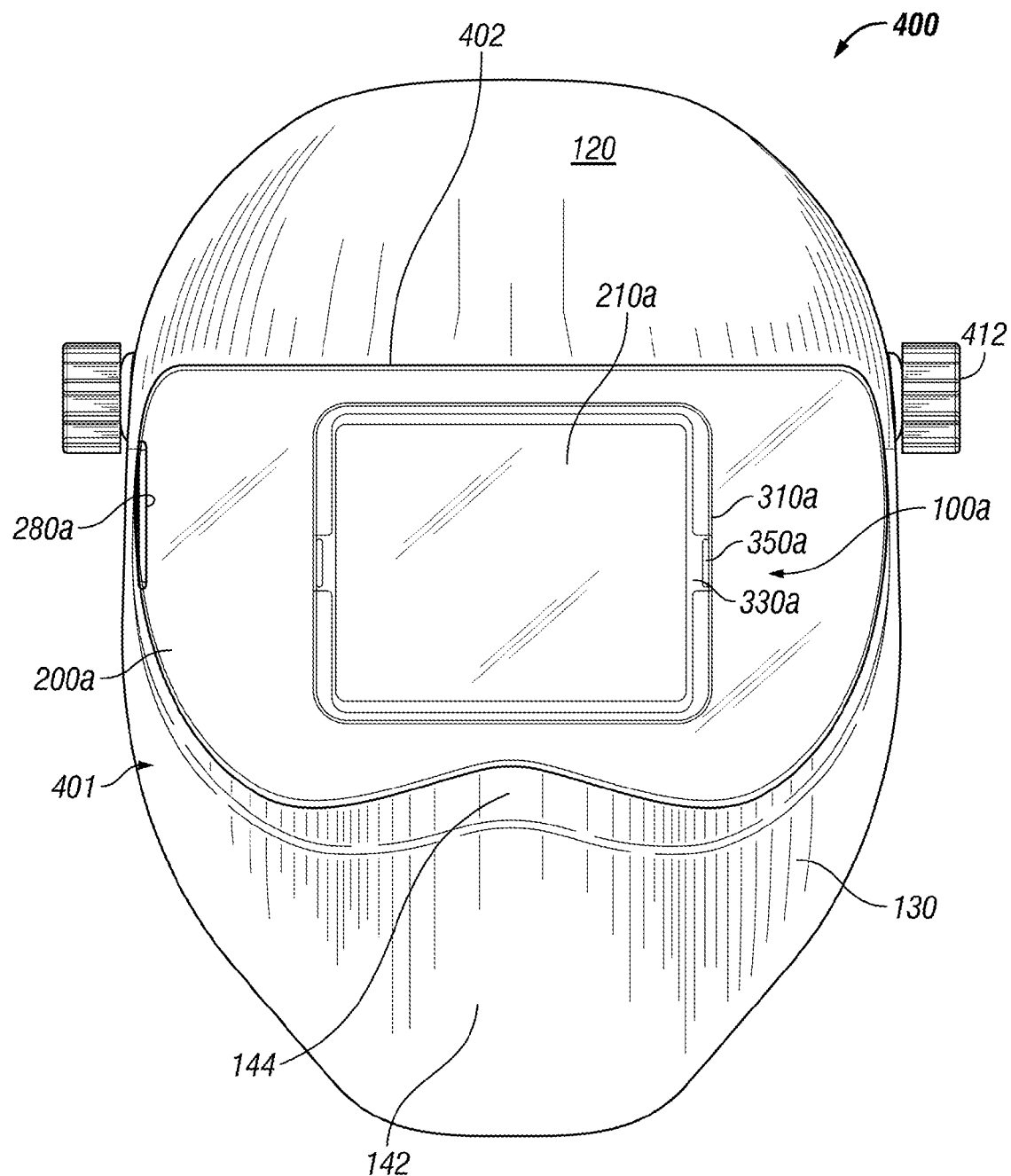
FIG. 14 is a front elevation view of the face protector of FIGS. 12 and 13.
Figure 15:
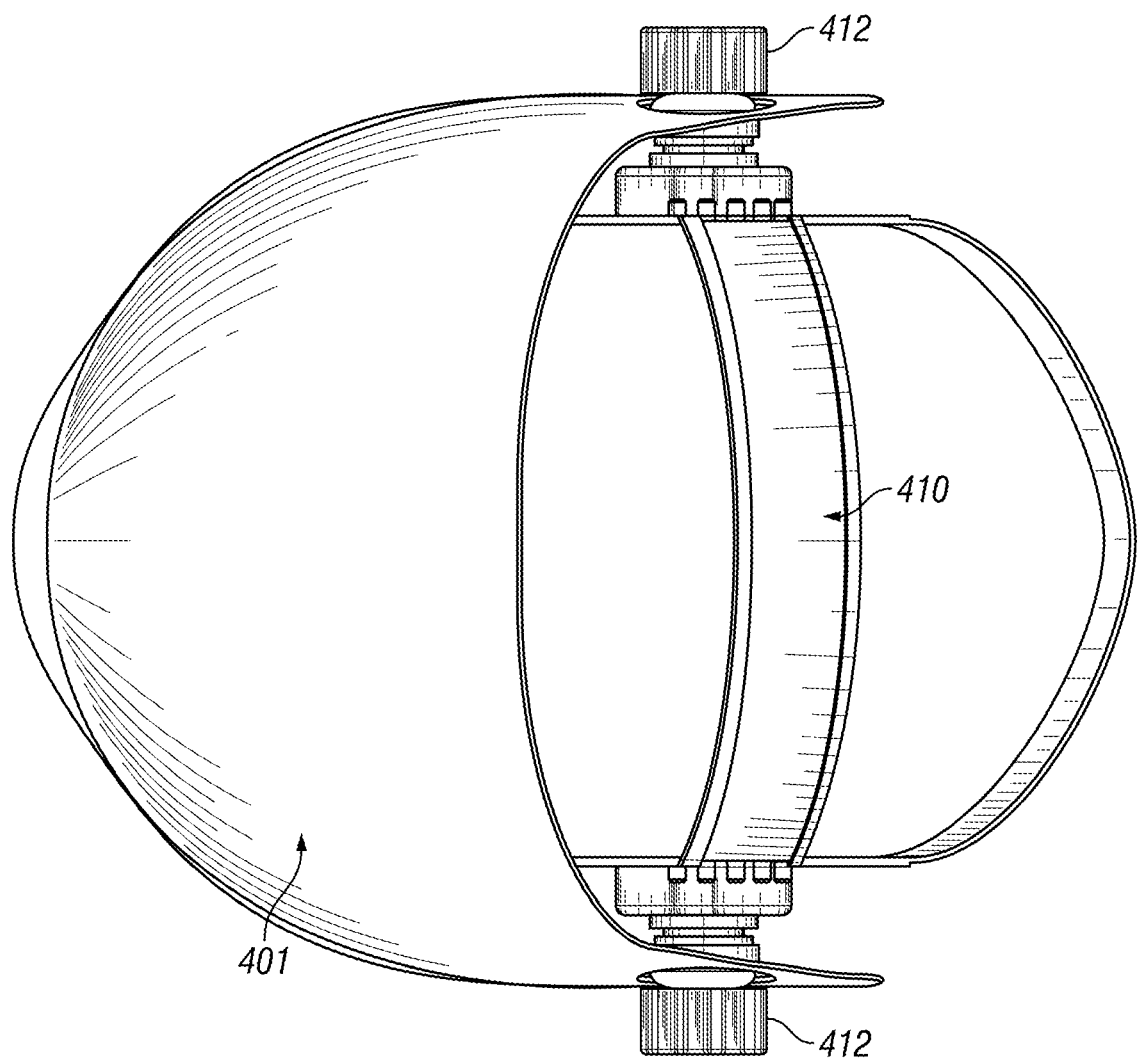
FIG. 15 is a top plan view of the face protector of FIGS. 12 to 14.
Figure 16:
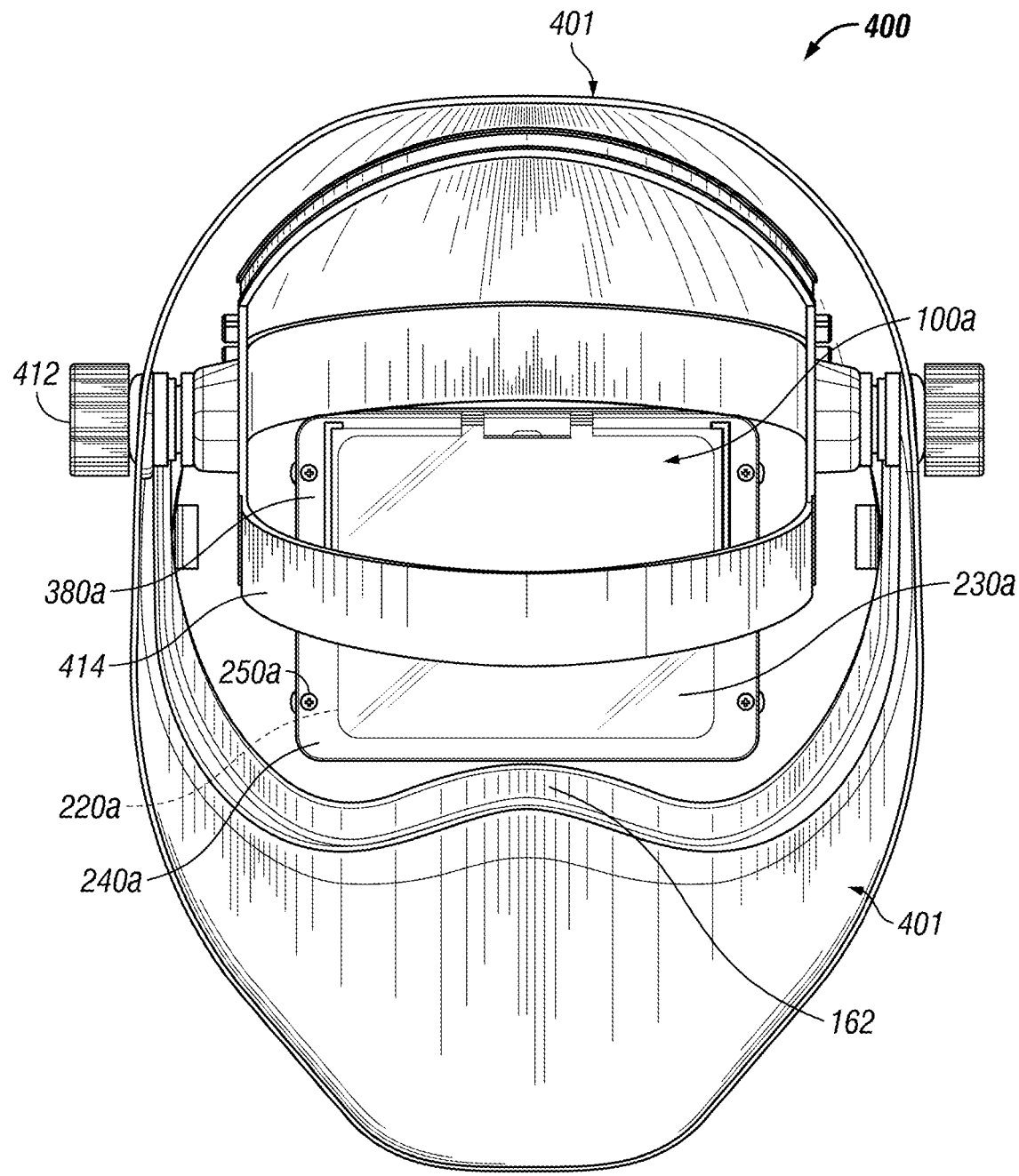
FIG. 16 is a rear elevation view of the face protector of FIGS. 12 to 15.
Figure 17:
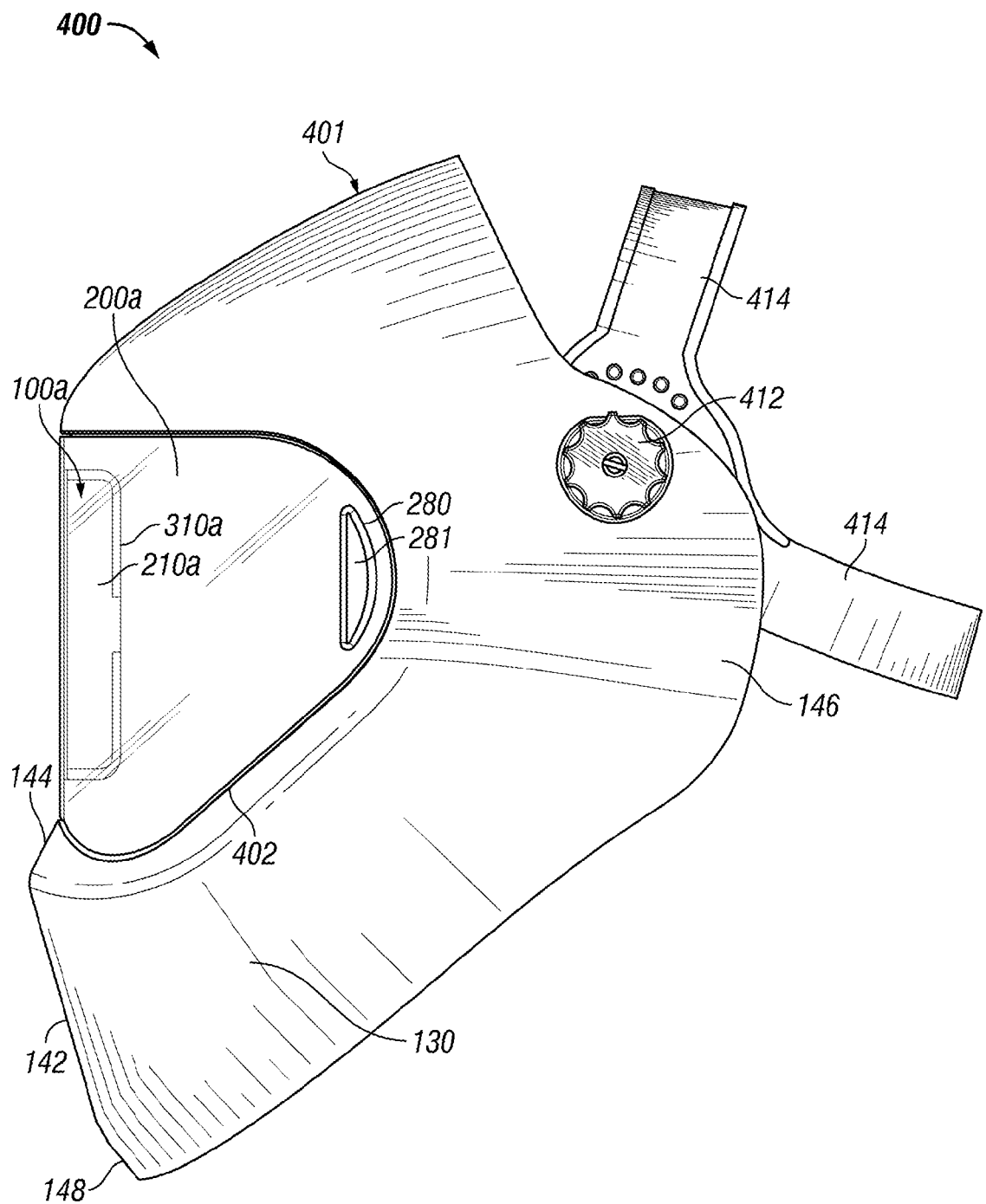
FIG. 17 is a right side elevation view of the face protector of FIGS. 12 to 16.
Figure 18:
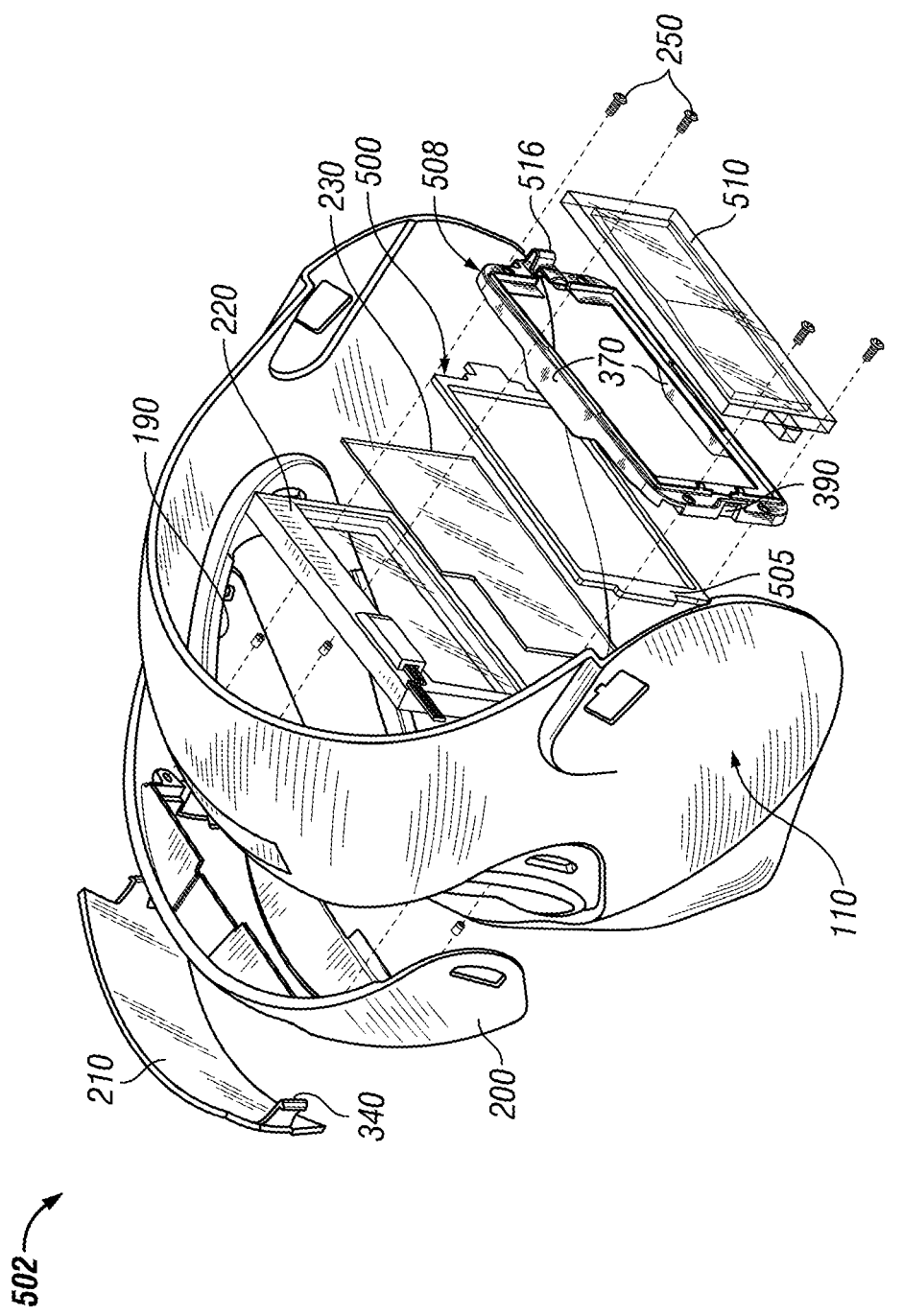
FIG. 18 is a rear exploded view of the face protector of FIGS. 1 to 9 with a modified lens-in-a-lens assembly (lens assembly) including an optional cheater or magnifying lens.

As can be seen by comparing FIGS. 9 and 14, the recessed front or eye opening 402 in the face plate 401 of this embodiment is larger than the recessed eye opening 300 of the first embodiment, and the ADF retainer lens 200a of the lens assembly is of shape and dimensions substantially matching those of opening 402 so that it is a close fit in the opening when opposite peripheral/temple portions 270a are secured to the opposite ear portions or side portions of the face plate. As in the previous embodiment, retainer lens 200a has crescent shaped holes 280a that overlap corresponding holes in the recessed eye opening section, and fasteners 281 extend through the overlapping holes to secure the retainer lens in the recessed opening. The retainer lens 200a is of increased height relative to the retainer lens 200 in the previous embodiment, so that it can accommodate a larger ADF lens 220a. As can be seen by comparing the rear end views of the face protectors 105 and 400 in FIGS. 7 and 16, respectively, the ADF lens 220a is of larger height than lens 220 but of substantially the same width, and may be of substantially square shape. The larger size of lenses 200a and 220a provides increased visibility to the user. The other parts of the lens assembly 100a which protect lens 220a and releasably secure the lens to retainer lens 200a are identical to those of the previous embodiment, apart from the increased dimensions of front cover 210a, lens protector 230a, and the frame or back cover 240a which holds lens 200a, as well as the front opening 310a in retainer lens 200, to accommodate the increased size of lens 220a. Apart from the change in dimensions, these parts are identical to the corresponding parts in the first embodiment and are therefore not described in any more detail.

The dimensions of the ADF lens 220a may be approximately 4.0 in.×4.0 in. or 4 in.×5 in., with the height dimensions of retainer lens 200a, the front opening 310a in the retainer lens, and the recessed opening 402 in the face plate in which lens 200a is mounted similarly scaled up to accommodate the increased size of lens 220a. As in the previous embodiment, lenses 200a and 220a may be of any selected initial lens shade and darkened lens shades, and lens 200a and 220a may be replaced or interchanged with other lenses of equivalent shapes and dimensions but different lens properties, as desired. As in the previous embodiment, lens assembly 100a may be modified by addition of a rear gasket similar to rear gasket 241 of FIGS. 10 and 11 but of larger dimensions to match the dimensions of ADF lens 220a. As in the embodiment of FIGS. 1 to 11, the addition of a rear gasket between rear cover 240a and lens protector 230a allows the user to select ADF lenses of different depths, including generic ADF lenses.

As in the previous embodiment, the lens-in-lens assembly 100a protects a wearer's eyes while allowing peripheral vision, and one or both lenses are replaceable or interchangeable as described above in connection with the first embodiment.

Another embodiment of a lens-in-a-lens assembly ("lens assembly") 500 of a face protector 502 is illustrated in FIGS. 18 to 22. Assembly 500 is of similar dimensions to the lens assembly 100 of FIGS. 1 to 9, but some of the parts are modified, as described in more detail below. Apart from the modifications to lens assembly 500, the face protector 502 is identical to the face protector of FIGS. 1 to 9, and like reference numbers are used for like parts as appropriate. As in the first embodiment, lens assembly 500 is configured for mounting in an eye opening 190 of face plate 110 of the face protector, and the remaining parts of the face protector including the face plate are identical to those of the first embodiment and are therefore not described in detail in connection with this embodiment. As described above, the face protector protects the front of a user's head (i.e., forehead, face, eyes, cheeks, jaw, chin, mouth, nose, ears) from flash burn, ultraviolet light, sparks, heat, and/or other elements associated with the activity/application.

As in the previous embodiments, the lens assembly 500 is replaceable/interchangeable with other lenses (e.g., for different welding applications as well as for other applications where face protection is needed). The lens assembly 500 includes an Automatic Darkening Filter ("ADF") retainer lens 200, a front cover 210, an ADF lens 220, a polycarbonate lens protector 230, a light block/spacer 505, a back cover or rear retainer frame 508, an optional cheater lens or magnifying glass 510, flat head screws 250, and threaded inserts 260.

Figure 19:
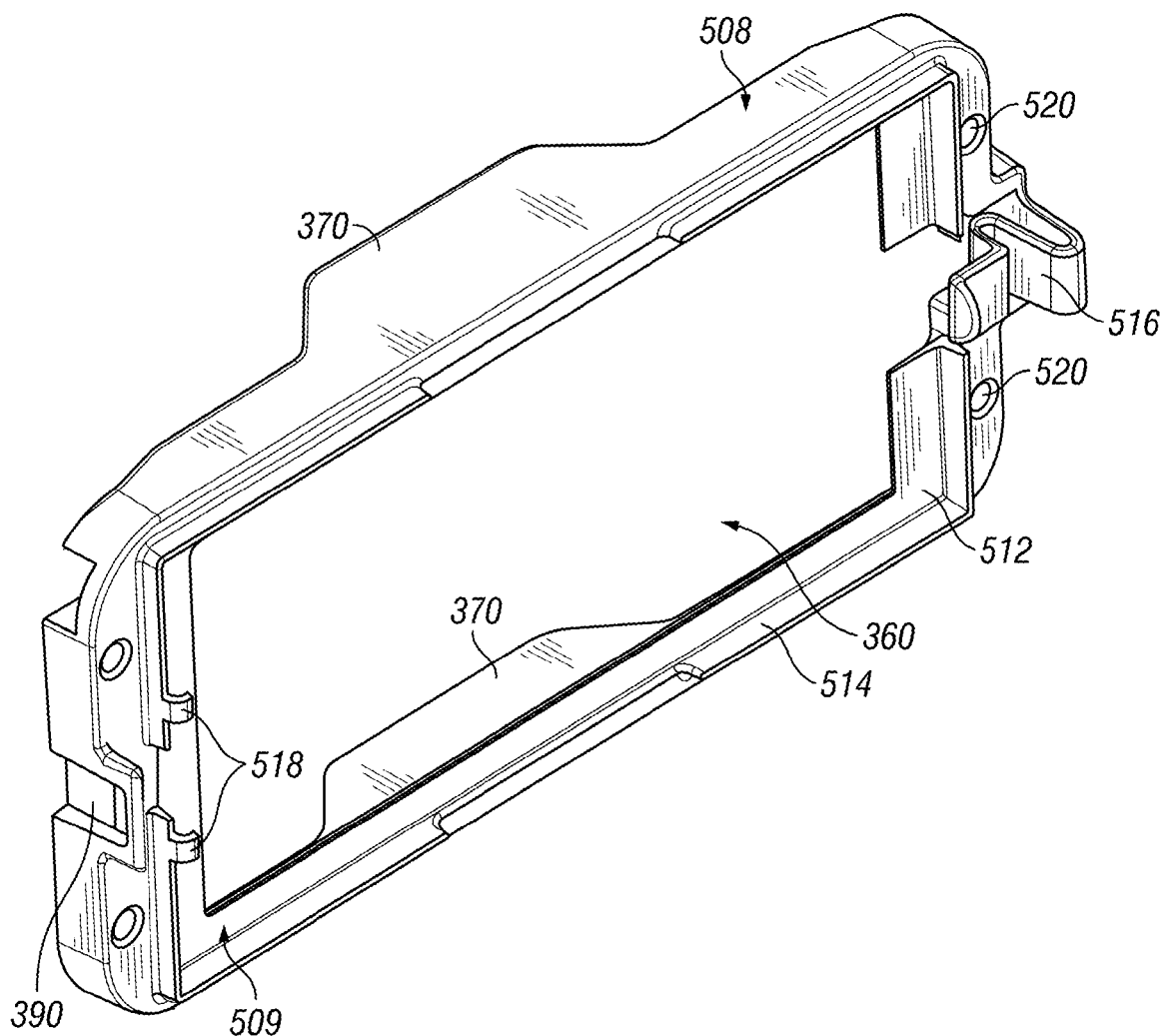
FIG. 19 is a rear perspective view of the modified back plate of the lens assembly of FIG. 18.
Figure 20:
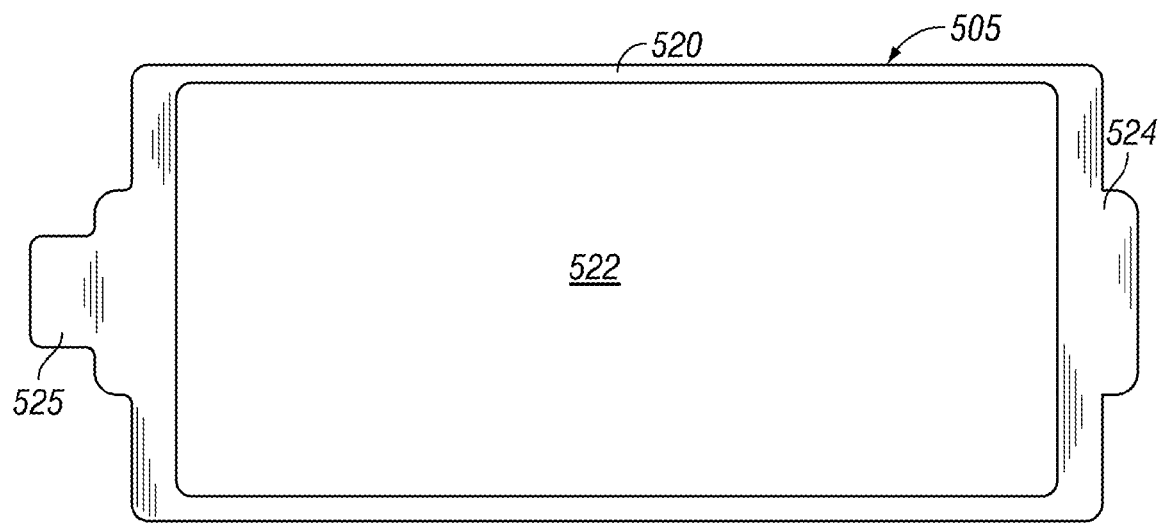
FIG. 20 is a front elevation view of the light block/spacer of the assembly of FIG. 18.
Figure 21:
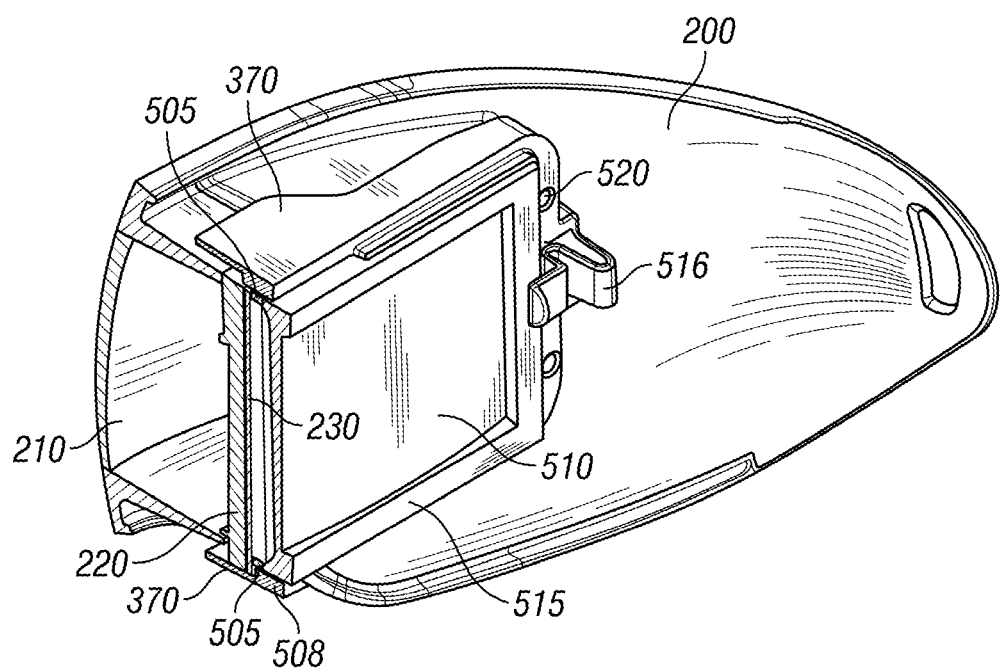
FIG. 21 is a rear perspective view, partially cut away, of the assembled lens assembly of FIG. 18.
Figure 22:
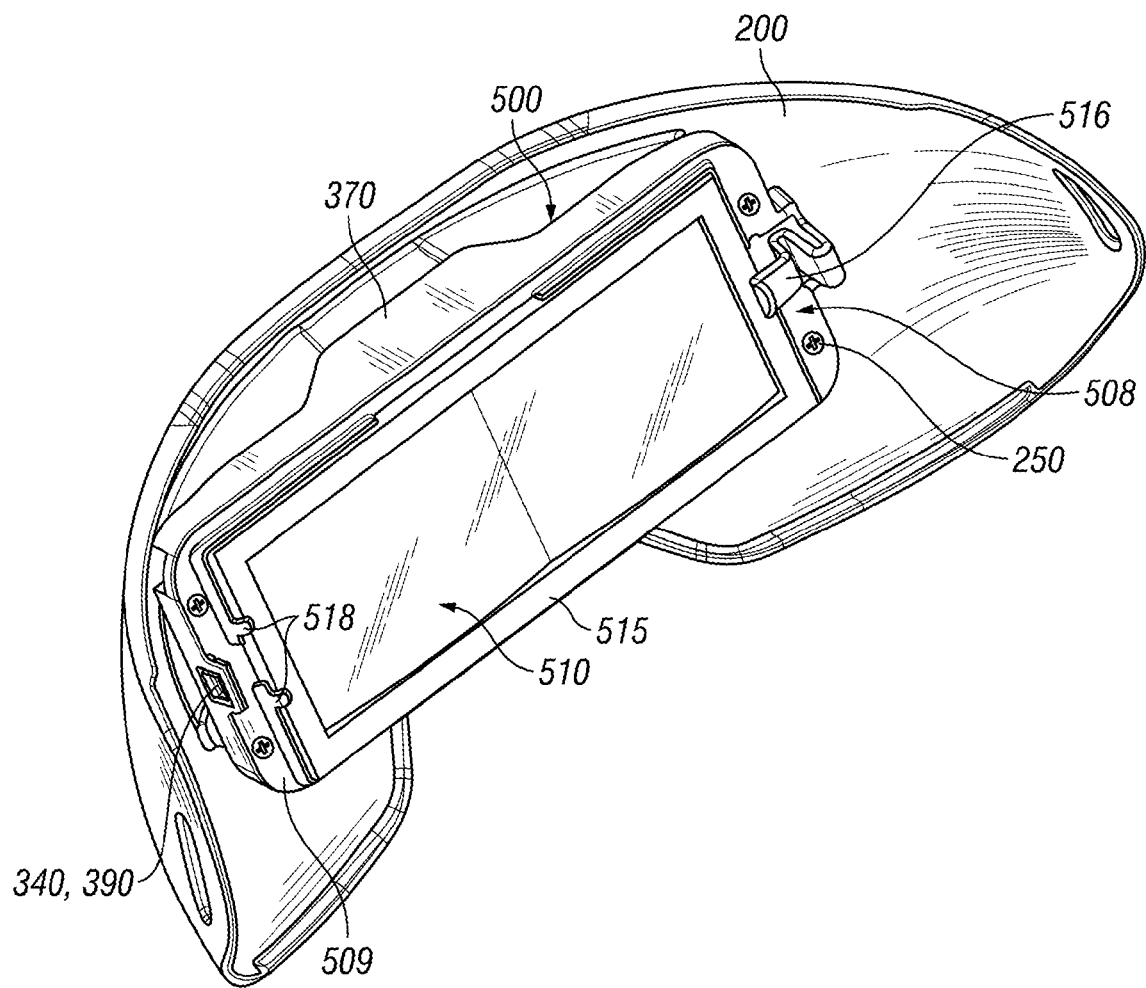
FIG. 22 is rear perspective view of the entire lens assembly when assembled, excluding other parts of the face protector.

In this embodiment, the back cover or retainer frame 508 is modified to accept cheater lens 510 and a light block/spacer 505 is added. Spacer 505 may be of resilient material to allow ADF lenses 220 of different depths to be secured in the assembly. The cheater lens or cheater glass 510 has a clear lens or magnifier similar to those used in off-the-shelf reading glasses, and a peripheral rectangular frame 515, and can be releasably attached to the back or outer face of back cover 508 when desired by the user of the face protector for additional magnification if needed while performing a task such as welding. As illustrated in FIG. 19, back cover 508 in this embodiment has a peripheral rectangular frame 509 with a recessed seat 512 against which the outer frame 515 of cheater lens 510 can be seated. Seat 512 is surrounded by rearwardly projecting rim 514 which has cut-outs around its perimeter. A fastener mechanism is located on the rear side of the frame for releasably attaching a selected cheater lens to the back of the frame. In the illustrated embodiment, the fastener mechanism comprises a spring clip or fastener 516 extending rearward from one side of the frame 509, and a pair of retainer tabs or hooks 518 located on the opposite side of frame 509. If a user wishes to use a cheater lens, they simply engage one side of the lens frame 515 under the two tabs 518, then push the other side past spring clip 516, which is depressed and then springs back over the opposite side of the lens frame to hold the cheater lens in position, as illustrated in FIGS. 21 and 22. The spring clip can be pulled up and released by the user in order to remove the cheater lens when it is no longer needed. Different cheater or magnifying lenses with different magnifications may be provided for selective attachment to the back cover as needed.

Other parts of the rectangular back cover 508 are similar to those of the first embodiment. Cover 508 includes a central rectangular opening 360 and upper/lower flange members 370 which extend forward from upper and lower portions of the frame 509, forming a recessed section in the front of the frame which receives/retains spacer 505, the polycarbonate lens protector 230 and the ADF lens 220, as best illustrated in FIG. 21. The light block/spacer 505 is illustrated in more detail in FIG. 20, and may be made of resilient material with light blocking properties. Spacer 505 has a rectangular peripheral frame 520 with a central opening 522. Frame 520 has light blocking projections 524, 525 projecting outwardly at its opposite sides.

The rearwardly extending latch projections 340 of the front cover 210 latch into the side cut-outs 390 of the back cover 508 when the parts are assembled (see FIG. 22), as in the first embodiment. The flat head screws 250 are inserted through holes 520 adjacent the corners of the frame 509 and threadably engage the threaded inserts 260 (FIG. 18) in the rear side of the ADF retainer lens 200 to connect/assemble the rectangular back cover 508, the spacer 505, the polycarbonate lens protector 230, the ADF lens 220, the ADF retainer lens 200, and the front cover 210 of the lens assembly 500 together.

Other parts of the assembly 500 have the same or substantially the same function and structure as described above in connection with the first embodiment. The ADF retainer lens 200 is partially spherical, toroidal, and/or cylindrical, providing the user with 180 degree viewing and unobstructed peripheral vision. Opposite peripheral/temple portions 270 of the ADF retainer lens 200 include crescent-shaped holes 280 that overlap crescent-shaped holes 290 in recessed eye opening section 300. Fasteners may extend through the holes 280, 290 for connecting the ADF retainer lens 200 to the recessed eye opening section 300 of the face plate 110. The ADF retainer lens 200 includes a central section with a rectangular opening 310 having front upper and lower recessed sections 320, side cut-outs 330, and rearwardly extending receiving section 335. The rearwardly extending receiving section 335 includes rearwardly extending upper horizontal member, lower horizontal member, and side vertical members that together form an air/space pocket between the ADF lens 220 and the front cover 210 when the lens assembly 500 is assembled, as illustrated in FIG. 21. In one embodiment, the ADF retainer lens 200 is a #10 shaded lens and is made of polycarbonate. In alternative embodiments, the ADF retainer lens 200 is a shaded lens in the range of #2-#12 shaded lens.

As in the first embodiment, the front cover 210 protects the ADF lens 220 from impact. The front cover 210 is transparent, un-shaded, rectangular/spherical/torical/cylindrical, made of polycarbonate and has a slight curved configuration/shape. Although front cover 210 is a separate component secured in an opening in the retainer lens in the illustrated embodiment, it may alternatively comprise a transparent or substantially transparent cover portion formed integrally with the retainer lens. The front cover 210, when disposed in the ADF retainer lens 200, is flush with the outer surface of lens 200. Rearward extending latch projections 340 extend from opposite sides 350 of the front cover 210 and extend through the side cut-outs 330 of the ADF retainer lens 200, as described above.

As indicated above, the lens assembly 500 has a lens-in-a-lens design with the ADF retainer lens 200 forming an outer holder lens and the ADF lens 220 forming an inner lens carried within/by the ADF retainer lens 200. Threaded inserts are injected/added into a rear/back side of the ADF retainer lens 200, as in the first embodiment (see FIG. 2).

The ADF lens 220 is substantially rectangular and has a rectangular frame portion and a rectangular lens portion held in the rectangular frame portion. In the embodiment shown, the ADF lens 220 is a 2 in.×4.25 in. ADF lens and is a shade #3 normally and darkens to shade #10 automatically when exposed to the flare of a welding arc. The ADF lens 220 is interchangeable with other 108 mm×50.8 mm×5 mm ADF filters and shades. In further embodiments, the outer ADF retainer lens 200 is a shade which matches the shade of the ADF lens 220, but these lenses may be of different shades in other embodiments. In an alternative embodiment, the ADF lens 220 in lens assembly 502 may be a 4 in.×4 in. or 4 in.×5 in. ADF lens, as described above in connection with the embodiment of FIGS. 10 to 15. In this alternative, the shape and dimensions of the other parts of the lens assembly, including spacer 505, back cover 508 and cheater lens 510, are modified appropriately for fitting together in the same way as illustrated for the rectangular lens of FIGS. 18 to 22. In further embodiments, the ADF lens 220 and/or the outer ADF retainer lens 200 may be made of different shades and/or different types of ADF lenses.

The above figures may depict exemplary configurations for the invention, which is done to aid in understanding the features and functionality that can be included in the invention. The invention is not restricted to the illustrated architectures or configurations, but can be implemented using a variety of alternative architectures and configurations. Additionally, although the invention is described above in terms of various exemplary embodiments and implementations, it should be understood that the various features and functionality described in one or more of the individual embodiments with which they are described, but instead can be applied, alone or in some combination, to one or more of the other embodiments of the invention, whether or not such embodiments are described and whether or not such features are presented as being a part of a described embodiment. Thus the breadth and scope of the present invention, especially in any following claims, should not be limited by any of the above-described exemplary embodiments.

Terms and phrases used in this document, and variations thereof, unless otherwise expressly stated, should be construed as open ended as opposed to limiting. As examples of the foregoing: the term "including" should be read as mean "including, without limitation" or the like; the term "example" is used to provide exemplary instances of the item in discussion, not an exhaustive or limiting list thereof; and adjectives such as "conventional," "traditional," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, a group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise. Furthermore, although item, elements or components of the disclosure may be described or claimed in the singular, the plural is contemplated to be within the scope thereof unless limitation to the singular is explicitly stated. The presence of broadening words and phrases such as "one or more," "at least," "but not limited to" or other like phrases in some instances shall not be read to mean that the narrower case is intended or required in instances where such broadening phrases may be absent.

The invention claimed is:

1. A face protector, comprising:
   a face plate having portions configured to protect the forehead, cheeks, jaw, chin, mouth, ears, and nose of a wearer, the face plate having a front opening configured for positioning over the eyes of a wearer and extending rearwardly over opposite sides of the face towards the ears of a wearer; and
   a lens-in-lens assembly secured in the front opening of the face plate;
   the lens-in-lens assembly comprising a first, retainer lens secured in the front opening and substantially flush with at least the forehead portion of the face plate, the first lens being of shape and dimensions which substantially match the shape and dimensions of the front opening, a second lens of smaller dimensions behind the first lens to provide a lens-in-a-lens configuration, a back cover behind the second lens, and a retainer assembly configured to releasably secure the second lens and back cover to the first lens; and
   at least one magnifying lens configured for selective releasable attachment to the lens-in-lens assembly behind the back cover, wherein the back cover comprises an outer frame and a fastener mechanism extending rearward from the outer frame and configured to releasably secure the magnifying lens to a rear face of the outer frame.

2. The face protector of claim 1, wherein the lens assembly further comprises a spacer between the back cover and second lens.

3. The face protector of claim 2, wherein the spacer comprises an outer frame with a central opening aligned with the second lens.

4. The face protector of claim 2, wherein the lens assembly further comprises an at least substantially transparent lens protector secured behind the second lens between the spacer and second lens.

5. The face protector of claim 2, wherein the spacer comprises a resilient gasket, whereby second lenses of different lens properties and different depths may be selectively secured behind the first lens.

6. The face protector of claim 1, wherein the outer frame has a recessed, rearwardly facing seat with a peripheral rim configured to receive the magnifying lens.

7. The face protector of claim 1, wherein the second lens is an automatic darkening filter (ADF) lens, and the first lens has a cover portion of at least substantially transparent material in front of the second lens.

8. The face protector of claim 7, wherein the first lens has a central opening in front of the second lens and the cover portion comprises a separate front cover member secured in the central opening.

9. The face protector of claim 1, wherein the first lens is releasably secured in the front opening of the face plate.

10. The face protector of claim 1, further comprising a set of interchangeable automatic darkening filter (ADF) second lenses of identical shape and different shades for selectively securing to the first lens.

11. The face protector of claim 1, wherein the first lens is curved and the second lens is at least substantially flat.

12. The face protector of claim 11 wherein the second lens is rectangular.

13. The face protector of claim 12, wherein the dimensions of the second lens are in the range from approximately 2 inches to 4.5 inches in height and approximately 4.0 to 5.0 inches in width.

14. The face protector of claim 11, wherein the first lens has a cover portion of rectangular peripheral shape aligned with the second lens, the cover portion being at least substantially transparent.

15. The face protector of claim 14, wherein the cover portion comprises a front cover member having an outer surface substantially flush with the first lens, and the first lens has an opening in which the cover member is secured.

16. The face protector of claim 14, wherein the first lens has a rearwardly extending receiving section adjacent the cover portion and the retainer assembly comprises releasable fasteners configured to releasably secure the second lens to the receiving section of the first lens.

17. A lens assembly for securing in an opening in a face plate of a face protector, comprising:
    a first, retainer lens configured to be secured in the front opening of a face plate and having a curvature substantially matching the curvature of the face plate, the first lens having a central portion extending across the face of a wearer of the face protector and side portions configured to provide peripheral vision to the wearer;
    a second lens of smaller dimensions behind the first lens to provide a lens-in-a-lens configuration;
    a back cover behind the second lens, the back cover comprising at least an outer frame; and
    releasable fasteners configured to releasably secure the back cover and second lens to the first lens; and
    at least one magnifying lens for selective, releasable attachment behind the back cover and the outer frame has a rearwardly projecting fastener mechanism configured for releasably securing the magnifying lens to the outer frame.

18. The lens assembly of claim 17, wherein the fastener mechanism comprises at least one spring clip configured for releasable snap engagement with an outer rim of the magnifying lens.

19. The lens assembly of claim 17, further comprising a plurality of magnifying lenses having different magnifications for selective, releasable attachment behind the back cover.

20. The lens assembly of claim 17, further comprising at least one spacer mounted between the second lens and back cover.

21. The lens assembly of claim 20, further comprising an at least substantially transparent lens protector secured between the second lens and spacer, the lens protector being of peripheral shape substantially matching the peripheral shape of the second lens.

22. The lens assembly of claim 20, wherein the spacer comprises an outer frame of elastomeric material having a central opening aligned with the second lens.

23. The lens assembly of claim 22, wherein the outer frame of the spacer has a pair of light blocking projections extending outwards from opposite sides of the frame.

24. The lens assembly of claim 17, further comprising at least one set of interchangeable lenses having different lens properties corresponding to one of said lenses, said one lens being releasably secured in said lens assembly and being interchangeable with other lenses in said one set of interchangeable lenses.

25. The lens assembly of claim 24, wherein the different lens properties comprise at least lens shade.

26. The lens assembly of claim 24, wherein said set of interchangeable lenses comprise automatic darkening filter (ADF) lenses of different shades.

27. The lens assembly of claim 17, further comprising first and second sets of interchangeable lenses having different lens properties and said first and second lenses are selected from the respective first and second set of interchangeable lenses.

28. The lens assembly of claim 17, further comprising a set of interchangeable second lenses having different lens properties for selectively securing between the first lens and back cover, at least some of said second lenses being of different depths, the assembly further comprising a spacer of flexible material between the second lens and back cover for accommodating second lenses of varying depth.

29. The lens assembly of claim 17, wherein the second lens is an automatic darkening filter (ADF) lens, and the first lens has a cover portion of at least substantially transparent material in front of the second lens.

30. A method of using a face protector with an interchangeable lens assembly, comprising:

securing a lens assembly in a front opening in a face plate configured to extend over the face of a wearer to protect the forehead, cheeks, jaw, chin, mouth, ears and nose of a wearer while the lens assembly protects the eyes and areas surrounding the eyes, the lens assembly having a first lens which fits the face plate front opening, a second lens of smaller dimensions behind the first lens, a back cover secured behind the second lens, at least one magnifying lens configured for selective releasable attachment behind the back cover, wherein the back cover comprises an outer frame and a fastener mechanism extending rearward from the outer frame and configured to releasably secure the magnifying lens to a rear face of the outer frame;

applying the assembled face protector to a wearer's head with the second lens extending in front of the wearer's eyes when looking forwards and the first lens extending over at least part of the sides of the wearer's face on each side of the wearer's eyes to provide peripheral vision to the wearer;

wearing the face protector during an activity; and removing the face protector after the activity.

31. The method of claim 30, further comprising releasably securing a selected magnifying lens behind the back cover before applying the assembled face protector to a wearer's head, whereby objects viewed by the wearer through the lens assembly are magnified.

* * * * *